United States Patent [19]

Häbich et al.

[11] Patent Number: 5,430,151

[45] Date of Patent: Jul. 4, 1995

[54] TRIFLUOROMETHYL-CONTAINING PSEUDOPEPTIDES ACTIVE AGAINST RETROVIRUSES

[75] Inventors: Dieter Häbich, Wuppertal; Wolfgang Röben, Bergisch Gladbach; Jutta Hansen, Wuppertal; Arnold Paessens, Haan, all of Germany

[73] Assignee: Bayer Aktiengesellschaft, Leverkusen, Germany

[21] Appl. No.: 920,216

[22] Filed: Jul. 24, 1992

[30] Foreign Application Priority Data

Aug. 10, 1991 [DE] Germany .................. 41 26 485.1

[51] Int. Cl.⁶ .................. C07D 211/06; C07D 207/04
[52] U.S. Cl. .................. 546/146; 546/147; 546/164; 546/233; 548/567; 548/568
[58] Field of Search .................. 548/528, 567, 568; 546/195, 233, 146, 147, 164; 514/319, 331, 428

[56] References Cited

U.S. PATENT DOCUMENTS

| | | | |
|---|---|---|---|
| 3,855,228 | 12/1974 | Bailey | 260/287 R |
| 3,927,000 | 12/1975 | Bailey | 260/283 R |
| 3,956,333 | 5/1976 | Bailey | 260/283 |

FOREIGN PATENT DOCUMENTS

| | | | |
|---|---|---|---|
| 0337714 | 10/1989 | European Pat. Off. | 514/428 |
| 0342541 | 11/1989 | European Pat. Off. | 514/428 |
| 0346847 | 12/1989 | European Pat. Off. | 514/428 |
| 0352000 | 1/1990 | European Pat. Off. | 514/428 |
| 0354522 | 2/1990 | European Pat. Off. | 514/319 |
| 0356223 | 2/1990 | European Pat. Off. | 514/319 |
| 0357332 | 3/1990 | European Pat. Off. | 514/319 |
| 0369141 | 5/1990 | European Pat. Off. | 514/319 |
| 0374098 | 6/1990 | European Pat. Off. | 514/319 |
| 0402646 | 12/1990 | European Pat. Off. | 514/331 |
| 2203740 | 10/1988 | United Kingdom | 514/428 |
| 9009191 | 8/1990 | WIPO | 514/331 |
| 9012804 | 11/1990 | WIPO | 514/331 |

OTHER PUBLICATIONS

Methods in Enzymology, vol. XXXIV, "Affinity Techniques, Enzyme Purification: Part B", Bovine Trypsin and Thrombin, Hixson, Jr. and A. H. Nishikawa, pp. 440–448, Academic Press; 1974.

Methods in Enzymology, vol. XXXIV, "Affinity Techniques, Enzyme Purification: Part B", Chymotrypsin(s), Tomlinson, et al., pp. 415–420, Academic Press 1974.

Affinity Chromatography, Biospecific Sorption; "Affinity Chromatography of Chymotrypsin on Soybean Trypsin Inhibitor Sepharose: Applications In Genetics And Nuclide Labelling", Gabel, Kasche, Amneus and Lundqvist, pp. 99–102, Pergamon Press, 1977.

Applied Microbiology and Biotechnology, Springer-Verlag 1979, Biotechnol. 6.; p. 195–(1979); "Recovery of Free Enzymes from Product Liquors by Bio-Affinity Adsorption: Trypsin Binding by Immobilised Soybean Inhibitor", Halling and Dunnill.

The Journal of Biological Chemistry, vol. 225, No. 15, Aug. 10, 1980, p. 7089, "Human Red Cell Purine Nucleoside Phosphorylase, Purification By Biospecific Affinity Chromatography and Physical Properties", Osborne, Mar. 17, 1980.

Hoppe-Seyler's Z. Physiol. Chem., vol. 361, p. 543, Apr. 1980, "Purification of Human and Bovine Alkaline Phosphatases by Affinity Chromatograph", Mossner, Boll and Pfleiderer.

(List continued on next page.)

Primary Examiner—C. Warren Ivy
Assistant Examiner—Zinna N. Davis
Attorney, Agent, or Firm—Sprung Horn Kramer & Woods

[57] ABSTRACT

The present invention relates to new trifluoromethyl-containing pseudopeptides of the general formula (I)

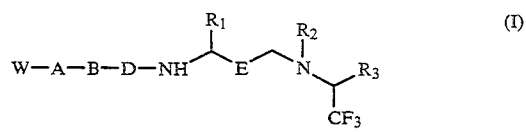

in which W, A, B, D, E, $R_1$, $R_2$ and $R_3$ have the meaning as outlined of their making and use as pharmaceuticals.

1 Claim, No Drawings

OTHER PUBLICATIONS

Analytical Biochemistry, vol. 107, p. 341, (1980), "Affinity Chromatographic Sorting of Carboxypeptidase A and its Chemically Modified Derivatives", Cueni, Bazzone, Riordan & Vallee, Mar. 31, 1980.

Hoppe-Seyler's Z. Physiol. Chem., vol. 359, p. 1019, Aug. 1978, "Affinity Chromatograph of Bovine Bran β-Hexosaminidases with Substrate As Affinity ligand"., Lisman and Overdijk, May 1978.

Biochem. J. (1978), vol. 175, p. 125, "Purification of the Hexokinases by Affinity Chromatography on Sepharose-N-Aminoacylglucosamine Derivatives", Wright, Warsy, Holroyde and Trayer, Feb. 1978.

Archives of Biochemistry and Biophysics, vol. 198, No. 2, Dec., 1979, p. 533, "Quantitative Affinity Chromatograph of α-Chymotrypsin", Dunn and Gilbert, Aug. 10, 1979.

Understanding Enzymes, Third Ed. (Horwood Press, 1991), pp. 309-310, Trevor Palmer.

P. Brongham et al., Synthesis (1987), 1015.

W. Adam et al., J. Org. Chem. 52, 2800 (1987).

R. Curci et al., J. Org. Chem 53, 3890 (1988).

J. Med. Chem. 34, 1225 (1991).

J. R. Luly et al., J. Org. Chem 52, (1987), 1487.

J. Org. Chem. 27, 1406 (1962).

J. Med. Chem. 32, 1371 (1989).

Hansen, J. Billich, S., Schylze, T., Sukrow, S. and Mölling, K. (1988), EMBO Journal, vol. 7, No. 6, pp. 1785-1791.

Journal of Virological Methods 20, 1988, 309-321.

H. Bühlmayer et al., J. Med. Chem. 31, 1839 (1988).

G. J. Hansen et al., J. Org. Chem. 50, 5399 (1985).

TRIFLUOROMETHYL-CONTAINING PSEUDOPEPTIDES ACTIVE AGAINST RETROVIRUSES

The invention relates to trifluoromethyl-containing pseudopeptides, processes for their preparation and their use as antiretroviral agents.

It has already been attempted to employ peptides and pseudopeptides, which in some cases also have renininhibiting activity, in the control of AIDS [cf. WO 90/09191; WO 90/12804; EP 393,445; EP 402,646; EP 373,576].

The present invention relates to new trifluoromethyl-containing pseudopeptides of the general formula (I)

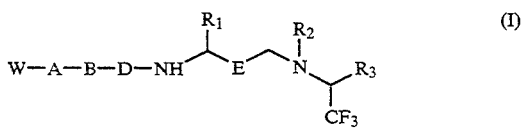

in which
W represents hydrogen or a typical amino protective group, or represents straight-chain or branched alkyl or alkenyl each having up to 6 carbon atoms which are optionally substituted by aryl having 6 to 10 carbon atoms or represents a group of the formula $R^4$—CO—, $R^5R^6N$—CO— or $R^7$—SO$_2$—,
in which
$R^4$ denotes hydrogen, trifluoromethyl or straight-chain or branched alkoxy having up to 8 carbon atoms or alkyl having up to 18 carbon atoms, each of which is optionally monosubstituted or disubstituted by identical or different substituents from the series comprising aryl having 6 to 10 carbon atoms and pyridyl, or denotes aryl having 6 to 10 carbon atoms, which is optionally substituted by halogen, trifluoromethyl, trifluoromethoxy or by straight-chain or branched alkyl having up to 8 carbon atoms, denotes cycloalkyl having 3 to 7 carbon atoms, or denotes quinolyl, quinolyl-N-oxide, indolyl, pyridyl, morpholino or piperazinyl, or denotes a radical of the formula

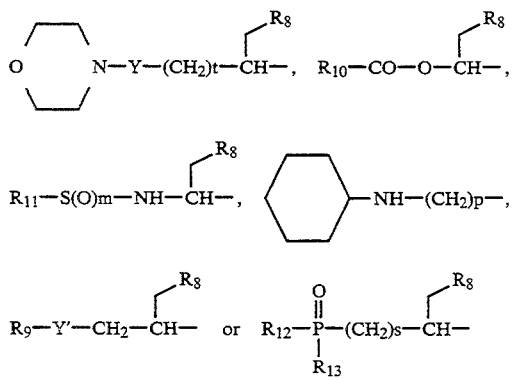

in which
$R^8$ denotes phenyl or naphthyl,
$R^9$ and $R^{10}$ independently of one another denote straight-chain or branched alkyl having up to 14 carbon atoms, which is optionally substituted by phenyl or naphthyl, or benzyloxy or aryl having 6 to 10 carbon atoms, which is in turn substituted by alkyl having up to 4 carbon atoms, $R^{11}$ has the abovementioned meaning of $R^9$ and $R^{10}$ and is identical to or different from this or denotes morpholino or pyrrolidinyl bonded via N,
m denotes a number 0, 1 or 2,
p denotes a number 1, 2 or 3,
Y and Y' independently of one another represent CO— or SO$_2$—,
t denotes a number 0, 1 or 2,
$R^{12}$ and $R^{13}$ independently of one another denote hydroxyl or alkoxy having up to 8 carbon atoms,
s denotes a number 1 or 2,
$R^5$ and $R^6$ independently of one another denote hydrogen or aryl having 6 to 10 carbon atoms, which can optionally be substituted by straight-chain or branched alkyl having up to 6 carbon atoms or by halogen, or denote cycloalkyl having 3 to 7 carbon atoms, or denote straight-chain or branched alkyl having up to 18 carbon atoms, which is optionally substituted by pyridyl,
$R^7$ denotes straight-chain or branched alkyl having up to 8 carbon atoms,
A, B and D are identical or different and represent a direct bond or represent a radical of the formula

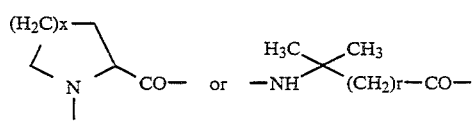

in which
x denotes the number 1 or 2 and
r denotes the number 0 or 1, or
represent a group of the formula

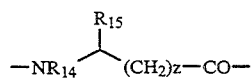

in which
z denotes the number 0 or 1,
$R^{14}$ denotes hydrogen or straight-chain or branched alkyl having up to 4 carbon atoms,
$R^{15}$ denotes cycloalkyl having 3 to 8 carbon atoms or aryl having 6 to 10 carbon atoms or hydrogen, or denotes straight-chain or branched alkyl having up to 8 carbon atoms,
where the alkyl is optionally substituted by cyano, methylthio, hydroxyl, mercapto or guanidyl or by a group of the formula —NR$^{16}$R$^{17}$ or R$^{18}$—OC—,
in which
$R^{16}$ and $R^{17}$ independently of one another represent hydrogen, straight-chain or branched alkyl having up to 8 carbon atoms or phenyl, and
$R^{18}$ denotes hydroxyl, benzyloxy, alkoxy having up to 6 carbon atoms or the abovementioned group —NR$^{16}$R$^{17}$,
or the alkyl is optionally substituted by cycloalkyl having 3 to 8 carbon atoms or by aryl having 6 to 10 carbon atoms, which in turn is substituted by hydroxyl, halogen, nitro or alkoxy having up to 8 carbon atoms or by the group —NR$^{16}$R$^{17}$,
in which
$R^{16}$ and $R^{17}$ have the abovementioned meaning, or the alkyl is optionally substituted by a 5- or 6-membered nitrogen-containing heterocycle or indolyl, in which the appropriate —NH functions are optionally protected by alkyl having up to 6 carbon atoms or by an amino protective group, R¹ represents straight-chain or branched alkyl or alkenyl having up to 10 carbon atoms which are optionally substituted by cycloalkyl having 3 to 8 carbon atoms or aryl having 6 to 10 carbon atoms, each of which can in turn be substituted by halogen, nitro, hydroxyl, amino or straight-chain or branched alkoxy having up to 4 carbon atoms, E represents a radical of the formula

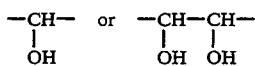

R² and R³ are identical or different and represent hydrogen or straight-chain or branched alkyl having up to 8 carbon atoms, or R² and R³, together with the nitrogen atom and including the

group, form a 5 - to 7-membered saturated heterocycle to which a further 5- to 6-membered, saturated, partially unsaturated or aromatic carbocycle can be fused, where both rings are optionally substituted by straight-chain or branched alkyl having up to 8 carbon atoms and their physiologically acceptable salts.

The compounds of the general formula (I) according to the invention have several asymmetric carbon atoms. They can exist independently of one another in the D- or L-form. The invention includes the optical antipodes as well as the isomer mixtures or racemates. Preferably, the groups A, B and D are present independently of one another in the optically pure form, preferably in the L-form.

The radical of the general formula (II)

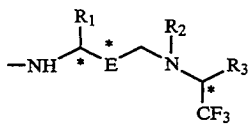

initially has, depending on the meaning of the radical E, at least 3 or 4 carbon atoms (*), where in the case of R² and R³ including the nitrogen atom forming a heterocyclic, optionally substituted ring system, the number of centres of asymmetry increases. The asymmetric carbon atoms can be present independently of one another in the R- or S-configuration.

Amino protective groups in the context of the invention are the customary amino protective groups used in peptide chemistry.

These preferably includes benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl methoxycarbonyl, ethoxycarbonyl, propoxycarbonyl, isopropoxycarbonyl, butoxycarbonyl, isobutoxycarbonyl, tert-butoxycarbonyl, allyloxycarbonyl, vinyloxycarbonyl, 3,4,5-trimethoxybenzyloxycarbonyl, cyclohexoxycarbonyl, 1,1-dimethylethoxycarbonyl, adamantylcarbonyl, phthaloyl, 2,2,2-trichloroethoxycarbonyl, 2,2,2-trichloro-tertbutoxycarbonyl, menthyloxycarbonyl, phenoxycarbonyl, 4-nitrophenoxycarbonyl, fluoroenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl or 4-nitrophenyl.

The compounds of the general formula (I) according to the invention can be present in the form of their salts. These can be salts with inorganic or organic acids or bases.

in which

W represents hydrogen, tert-butoxycarbonyl (BOC), 9-fluorenylmethoxycarbonyl (Fmoc), benzyloxycarbonyl (Z) or pyridylmethoxycarbonyl, or represents straight-chain or branched alkyl or alkenyl each having up to 4 carbon atoms which are optionally substituted by phenyl, or represents a group of the formula R⁴—CO—, R⁵R⁶N—CO— or R⁷SO₂— in which

R⁴ denotes hydrogen, trifluoromethyl or straight-chain or branched alkoxy having up to 6 carbon atoms or alkyl having up to 16 carbon atoms, each of which can optionally be monosubstituted or disubstituted by identical or different substituents from the series comprising phenyl, naphthyl and pyridyl, or denotes phenyl or naphthyl, each of which can optionally be substituted by fluorine, chlorine, trifluoromethyl or trifluoromethoxy or by straight-chain or branched alkyl having up to 6 carbon atoms, cyclopropyl, cyclopentyl, cyclohexyl, quinolyl, quinolyl-N-oxide, indolyl, pyridyl, morpholino or piperazinyl, or denotes a radical of the formula

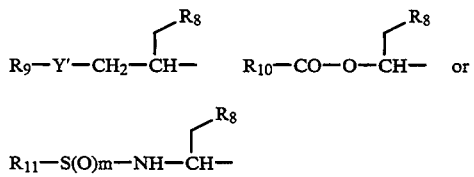

in which

Y' denotes the CO or SO₂ group,

R⁸ denotes phenyl or naphthyl,

R⁹ and R¹⁰ independently of one another denote straight-chain or branched alkyl having up to 8 carbon atoms, tolyl, benzyloxy, phenyl or naphthyl, R¹¹ has the abovementioned meaning of R⁹ and R¹⁰ and is identical to or different from this or denotes morpholino or pyrrolidinyl bonded via N, m denotes a number 1 or 2, R⁵ and R⁶ independently of one another denote hydrogen or phenyl or naphthyl, each of which can optionally be substituted by straight-chain or branched alkyl having up to 4 carbon atoms, fluorine or chlorine, denote cyclopropyl, cyclopentyl or cyclohexyl, or denote straight-chain or branched alkyl having up to 16 carbon atoms, which is optionally substituted by pyridyl, R⁷ denotes straight-chain or branched alkyl having up to 6 carbon atoms, A, B and D independently of one another represent a direct bond or represent proline, or represent a radical of the formula $$\underset{-NH}{\overset{H_3C\diagup\diagdown CH_3}{|}}(CH_2)_r-CO-$$

in which r denotes the number 0 or 1 represent a group of the formula $$-NR_{14}\overset{R_{15}}{\underset{|}{\diagdown}}(CH_2)_z-CO-$$

in which z denotes the number 0 or 1, $R^{15}$ denotes cyclopentyl, cyclohexyl, phenyl or hydrogen, or straight-chain or branched alkyl having up to 6 carbon atoms, where the alkyl can optionally be substituted by cyano, methylthio, hydroxyl, mercapto, guanidyl, amino, carboxyl or $H_2N-CO-$, or the alkyl can be substituted by cyclohexyl, naphthyl or phenyl, which can in turn be substituted by fluorine, hydroxyl, nitro or alkoxy having up to 4 carbon atoms, or the alkyl is substituted by indolyl, imidazolyl, pyridyl, triazolyl or pyrazolyl, where the appropriate —NH functions are optionally protected by alkyl having up to 4 carbon atoms or by an amino protective group, $R^1$ represents a straight-chain or branched alkyl or alkenyl having up to 8 carbon atoms, which are optionally substituted by cyclopropyl, cyclobutyl, cyclopentyl, cyclohexyl, cycloheptyl or phenyl which can in turn be substituted by fluorine, chlorine, bromine, nitro, hydroxyl or amino E represents a radical of the formula $$\underset{OH}{\overset{|}{-CH-}} \quad \text{or} \quad \underset{OH\ OH}{\overset{|\ \ |}{-CH-CH-}}$$

$R^2$ and $R^3$ are identical or different and represent hydrogen or straight-chain or branched alkyl having up to 6 carbon atoms, or $R^2$ and $R^3$ together with the nitrogen atom and including the $$\underset{CF_3}{\overset{|}{-CH-}}$$

group represent a radical of the formula

[structures depicting pyrrolidine, piperidine, tetrahydroisoquinoline, decahydroquinoline, decahydroisoquinoline variants each bearing a CF₃ substituent, and an N-methylpyrrolidine with CF₃]

where both rings are optionally substituted by straight-chain or branched alkyl having up to 6 carbon atoms and their physiologically acceptable salts.

Particularly preferred compounds of the general formula (I) are those in which

W represents hydrogen, tert-butoxycarbonyl (BOC), benzyloxycarbonyl (Z) or pyridylmethoxycarbonyl, or represents allyl or benzyl, represents a group of the formula $R^4-CO-$, $R^5R^6N-C-$ or $R^7-SO_2-$, in which $R^4$ denotes hydrogen or straight-chain or branched alkoxy having up to 4 carbon atoms, alkyl having up to 14 carbon atoms, which can optionally be monosubstituted or disubstituted by phenyl, napthyl or pyridyl, or denotes phenyl or naphthyl, each of which can optionally be substituted by fluorine, chlorine, trifluoromethyl or trifluoromethoxy or by straight-chain or branched alkyl having up to 4 carbon atoms, denotes cyclopropyl, cyclopentyl, cyclohexyl, quinolyl, quinolyl-N-oxide, indolyl, pyridyl, morpholino or piperazinyl, or denotes a radical of the formula $$R_9-Y'-CH_2-\underset{|}{\overset{R_8}{CH}}- \quad \text{or} \quad R_{11}-S(O)_m-NH-\underset{|}{\overset{R_8}{CH}}-$$

in which

Y' denotes the CO or $SO_2$ group, $R^8$ denotes phenyl or naphthyl $R^9$ denotes straight-chain or branched alkyl having up to 4 carbon atoms, tolyl, benzyloxy, phenyl or naphthyl, $R^{11}$ has the abovementioned meaning of $R^9$ and is identical to or different from this or denotes morpholino or pyrrolidinyl bonded via N, m denotes the number 2, $R^5$ and $R^6$ independently of one another denote hydrogen or denote phenyl or naphthyl, which are optionally substituted by methyl, fluorine or chlorine, denote cyclopropyl, cyclopentyl or cyclohexyl, denote straight-chain or branched alkyl having up to 14 carbon atoms, which is optionally substituted by pyridyl, $R^7$ denotes straight-chain or branched alkyl having up to 4 carbon atoms, A, B and D independently of one another represent a direct bond, proline or represent a radical of the formula $$\begin{array}{c} H_3C \quad CH_3 \\ -NH \quad CO- \end{array} \text{ or,}$$

represent a group of the formula $$-NR_{14}\overset{R_{15}}{\underset{}{\mathrm{C}}}(CH_2)_z-CO-,$$

which
denotes the number 0 or 1,
$R^{14}$ denotes hydrogen or methyl,
$R^{15}$ denotes cyclopentyl, cyclohexyl or hydrogen, or denotes straight-chain or branched alkyl having up to 4 carbon atoms,
where the alkyl can optionally be substituted by cyano, methylthio, hydroxyl, mercapto, guanidyl, amino, carboxyl or $H_2N-CO-$,
or the alkyl can be substituted by cyclohexyl, naphthyl or phenyl, which can in turn be substituted by fluorine, chorine or alkoxy having up to 4 carbon atoms,
or the alkyl is substituted by indolyl, imidazolyl, triazolyl, pyridyl or pyrazolyl, where the NH function is optionally protected by methyl, benzyloxymethylene or tert-butyloxycarbonyl $R^1$ represents a straight-chain or branched alkyl having up to 6 carbon atoms, which is optionally substituted by cyclopropyl, cyclopentyl, cyclohexyl or phenyl which can in turn be substituted by hydroxyl, E represents a radical of the formula $$\begin{array}{cc} -CH- & -CH-CH- \\ | & \text{or} \quad | \quad | \\ OH & OH \quad OH \end{array}$$

$R^2$ and $R^3$ are identical or different and represent hydrogen or straight-chain or branched alkyl having up to 4 carbon atoms, or $R^2$ and $R^3$ together with the nitrogen atom and including the $$\begin{array}{c} -CH- \\ | \\ CF_3 \end{array}$$

group represent a radical of the formula

[structures: pyrrolidine-CF3, piperidine-CF3, tetrahydroisoquinoline-CF3]

-continued

[structures: tetrahydroisoquinoline-CF3, decahydroquinoline-CF3, decahydroisoquinoline-CF3, methylpyrrolidine-CF3, octahydroisoquinoline-CF3]

and their physiologically acceptable salts.

In addition, processes for the preparation of the compounds of the general formula (I) according to the invention have been found, characterised in that in the case in which E represents the $$\begin{array}{c} -CH- \\ | \\ OH \end{array}$$

group,

[A] either compounds of the general formula (III)

$$W'-A'-B'-D'NH\overset{R_1}{\underset{}{\diagdown}}\diagup \qquad (III)$$

in which $R^1$ has the abovementioned meaning,

A', B', and D' have the abovementioned meaning of A, B and D but do not simultaneously represent a bond and W' has the abovementioned meaning of W but does not represent hydrogen, are first converted using an epoxidation reaction, if appropriate with the aid of a base or of a phase transfer catalysis, into the compounds of the general formula (IV)

$$W'-A'-B'-D'NH\overset{R_1}{\underset{O}{\diagdown}}\diagup \qquad (IV)$$

in which

W', A', B', D' and $R^1$ have the abovementioned meaning, and the latter are then reacted with compounds of the general formula (V)

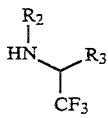

in which

R[2] and R[3] have the abovementioned meaning, in inert solvents and, if appropriate, the protective group W' is removed (W=H) or replaced, or

[B] compounds of the general formula (IVa)

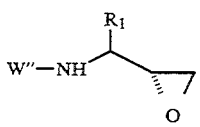

in which

R[1] has the abovementioned meaning and

W''' represents an amino protective group, preferably BOC or Z, are first converted directly by reaction with compounds of the general formula (V) into the compounds of the general formula (VI)

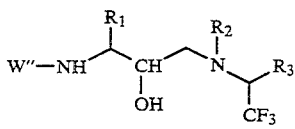

in which

W''', R[1] R[2] and R[3] have the abovementioned meaning, and then the latter are either condensed in inert solvents with compounds of the general formula (VII), (VIIa), (VIII) or (VIIIa)

W'—A—B—D—OH (VII); W'—A'—B'—D'—OH (VIIa); W—X (VIII); or (G)₂O (VIIIa)

in which

W, W', A, A', B, B', D and D' have the abovementioned meaning

X, depending on the meaning of the substituent W, represents hydroxyl or halogen, preferably chlorine, and G represents the CF₃CO— or H₃C—CO group, in the case of the compounds of the general formula (VII) or (VIIa) by the conditions customary in peptide chemistry with activation of the carboxylic acid, if appropriate in the presence of a base and of an auxiliary, and respective removal of the protective groups, in one step (VIIa) or successively (VII), and if appropriate the substituent W is varied by customary methods, and in the case in which E represents the

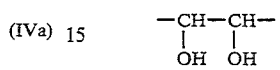

group

[C] compounds of the general formula (IX)

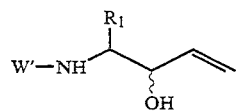

in which

W' and R[1] have the abovementioned meaning, are first converted using the epoxidation reaction described under [A] into the compounds of the general formula (X)

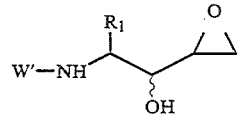

in which

W' and R[1] have the abovementioned meaning, these are reacted with the compounds of the general formula (V) with ring opening and then as described under [B] with the compounds of the general formula (VII), (VIIa), (VIII) and/or (VIIIa), and if appropriate a separation of the diastereomers is carried out.

The processes according to the invention can be illustrated by way of example by the following equations:

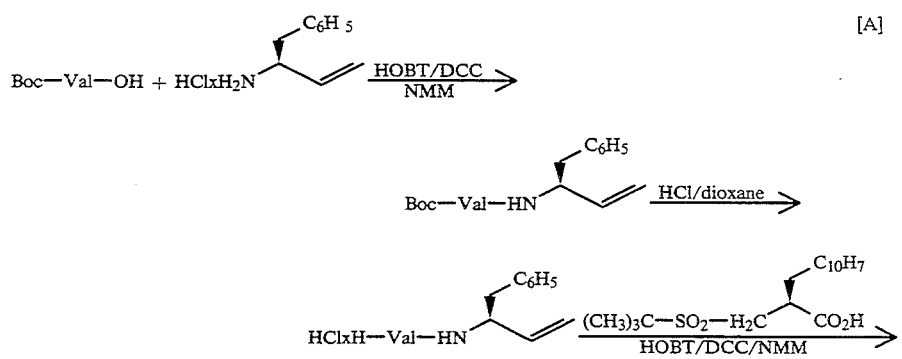

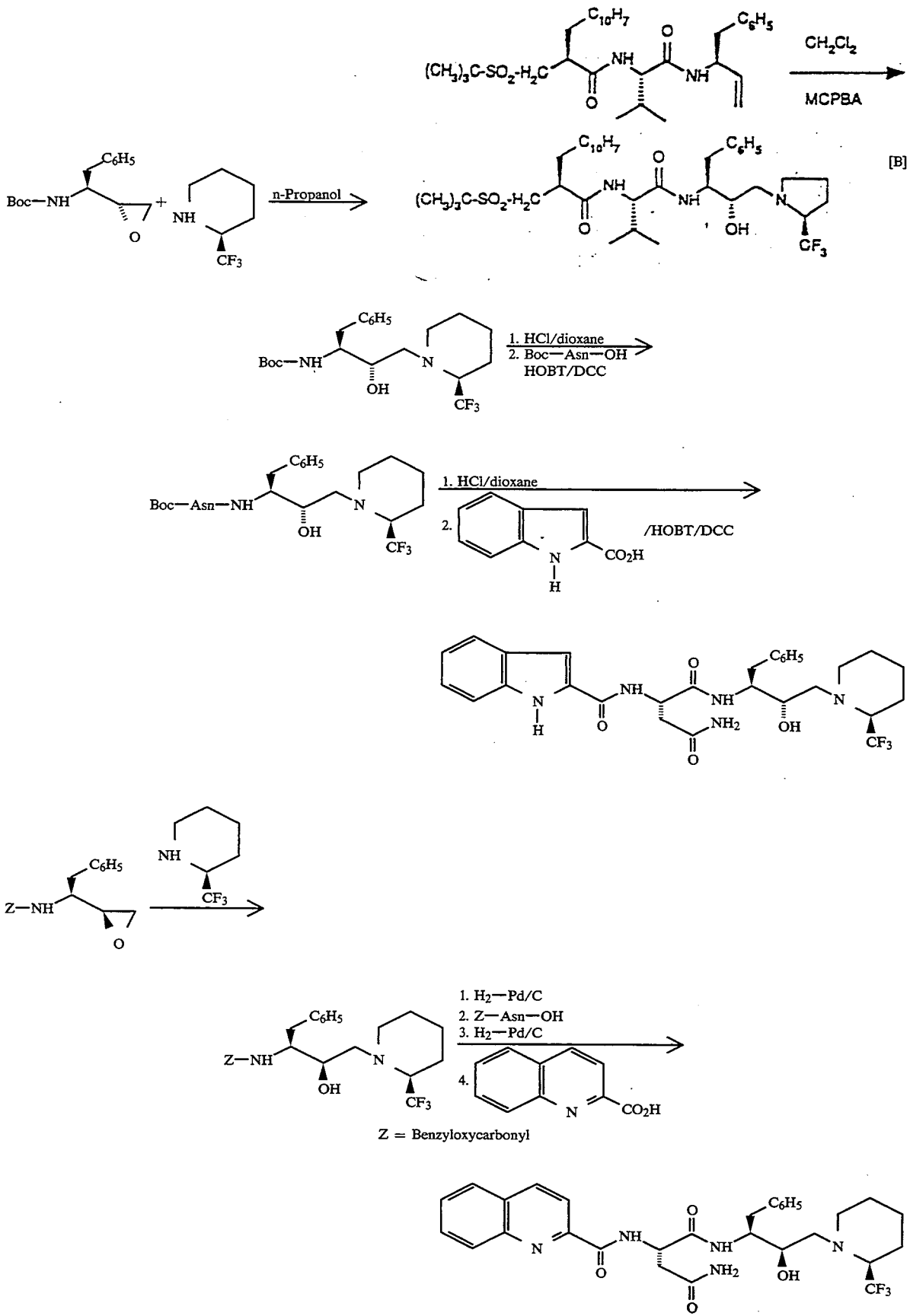

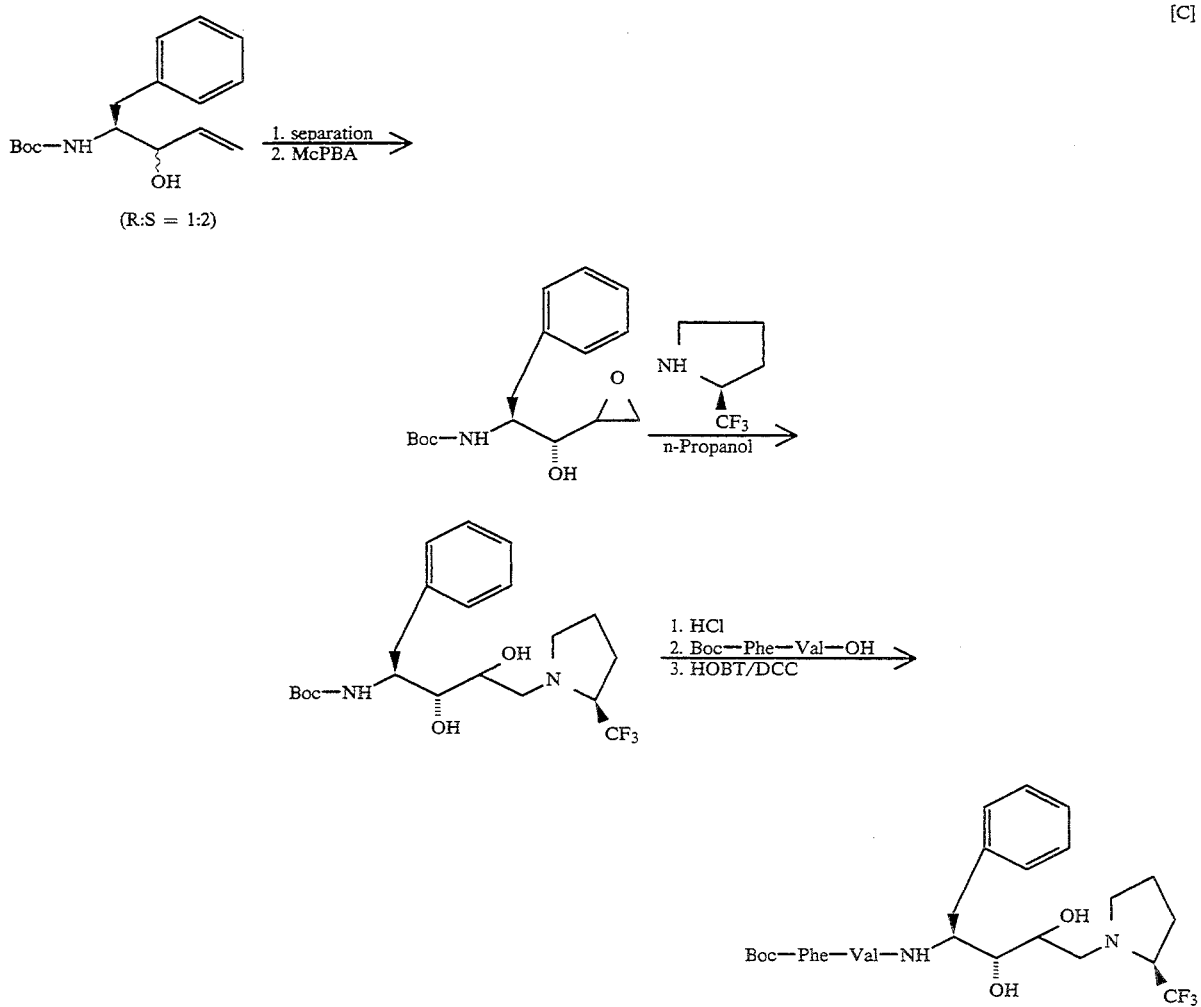

Suitable solvents are the customary organic solvents which do not change under the reaction conditions. These preferably include organic solvents such as alcohols, for example methanol, ethanol or n-propanol, ethers, for example diethyl ether, glycol monomethyl ether or glycol dimethyl ether, dioxane or tetrahydrofuran, or hydrocarbons such as benzene, toluene, xylene, cyclohexane or mineral oil fractions or halogenohydrocarbons such as methylene chloride, dichloroethane (DCE), chloroform, carbon tetrachloride, or dimethyl sulfoxide, dimethylformamide, hexamethylphosphoric triamide, ethyl acetate, pyridine, triethylamine or picoline. It is also possible to use mixtures of the solvents mentioned. Dichloromethane, dichloroethane, dimethylformamide or npropanol are particularly preferred.

Suitable reagents for the epoxidation are the compounds known from the literature such as, for example, m-chloroperbenzoic acid, magnesium monoperoxyphthalate, dimethyldioxirane or methyl(trifluoromethyl)-dioxirane. m-Chloroperbenzoic acid and magnesium monoperoxyphthalate are preferred [cf. P. Brongham et al., Synthesis (1987), 1015; W. Adam et al., J. Org. Chem. 52, 2800 (1987) and R. Curci et al., J. Org. Chem. 53. 3890 (1988)].

If the epoxidation is carried out with the aid of a phase transfer catalysis, auxiliaries employed are, for example, organic ammonium chlorides or bromides such as, for example, benzyltriethylammonium chloride or bromide, methyltrioctylammonium chloride, tetrabutylammonium bromide, tricaprylmethylammoniumchloride (Aliquat 336). Benzyltriethylammonium chloride and bromide are preferred.

The epoxidation is carried out in a temperature range from −10° C. to +90° C., preferably from 0° C. to +60° C.

The reactions can be carried out either at normal pressure or at elevated or reduced pressure (for example 0.5 to 5 bar), preferably at normal pressure.

The compounds of the general formula (III) and (IIIa) are known in some cases or are new and can be prepared by a process in which

[D] compounds of the general formula (XI)

$$\underset{H_2N}{\overset{R_1}{\diagdown}}\diagup\!\!\!\diagdown \qquad (XI)$$

in which

R$^1$ has the abovementioned meaning, are reacted with compounds of the general formula (VIIa)

in which

W', A', B' and D' have the abovementioned meaning, with activation of the carboxylic acid, if appropriate in the presence of a base and of an auxiliary, in one step or successively (depending on the meaning of the substituents A', B' and D'), or

[E] compounds of the general formula (IIIa)

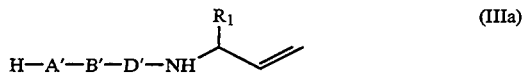

in which

A', B', D' and $R^1$ have the abovementioned meaning, are reacted with compounds of the general formula (VIII) or (VIIIa) by the conditions customary in peptide chemistry in inert solvents, if appropriate in the presence of a base with the introduction of the protective group (W' or W").

Suitable solvents for all process steps are the customary inert solvents which do not change under the reaction conditions. These preferably include organic solvents such as ethers, for example diethyl ether, glycol monomethyl ether or glycol dimethyl ether, dioxane or tetrahydrofuran, or hydrocarbons such as benzene, toluene, xylene, cyclohexane or mineral oil fractions or halogenohydrocarbons such as methylene chloride, chloroform, carbon tetrachloride, or dimethyl sulfoxide, dimethylformamide, hexamethylphosphoric triamide, ethyl acetate, pyridine, triethylamine or picoline. It is also possible to use mixtures of the solvents mentioned. Dichloromethane, dimethyl formamide or tetrahydrofuran are particularly preferred.

A few compounds of the general formulae (III) and (IIIa) are known from the literature [cf. J. Med. Chem. 34, 1225 (1991)].

The compounds of the general formulae (VII) and (VIIa) are known per se and can be prepared by reaction of an appropriate fragment, consisting of one or more amino acid groups, containing a free carboxyl group, if appropriate present in activated form, with a complementary fragment, consisting of one or more amino acid groups, if appropriate in activated form, and by repeating this process with appropriate fragments; then, if appropriate, protective groups can be removed or replaced by other protective groups [cf. Houben-Weyl, Methoden der organischen Chemie (Methods of Organic Chemistry), Synthesis of peptides II, 4th edition, Vol. 15/1, 15/2, Georg Thieme Verlag, Stuttgart].

Auxiliaries employed for the respective peptide couplings and the introduction of the radical W (VIII) and (VIIIa) are preferably condensing agents which can also be bases, in particular if the carboxyl group is present in activated form as the anhydride. Preferred condensing agents here are the customary condensing agents such as carbodiimides, for example N,N'-diethyl-, N,N'-diisopropyl or N,N'-dicyclohexylcarbodiimide, N-(3-dimethylaminoisopropyl)-N'-ethylcarbodiimide hydrochloride, N-cyclohexyl-N'-(2-morpholinoethyl)-carbodiimide metho-p-toluenesulphonate (CMCT) or carbonyl compounds such as carbonyldiimidazole, or 1,2-oxazolium compounds such as 2-ethyl-5-phenyl-1,2-oxazolium-3-sulphate or 2-tert-butyl-5-methyl-isoxazolium perchlorate, or acylamino compounds such as 2-ethoxy-1-ethoxycarbonyl-1,2dihydroquinoline, or propane phosphonic anhydride, or isobutyl chloroformate, or benzotriazolyloxytris(dimethylamino)phosphonium hexafluorophosphate or 1-hydroxybenzotriazole.

The compounds of the general formula (XI) are known per se or can be prepared by methods known from the literature [cf. J.R. Luly et al., J. Org. Chem. 52, (1987), 1487].

With a few exceptions [cf. J. Med. Chem. 34, 1225, (1991)], the compounds of the general formula (IV) are new and can be prepared by the abovementioned process.

The compounds of the general formula (V), in the case in which $R^2$ and $R^3$ each represent an open-chain radical defined above, are known in some cases [cf. J. Org. Chem. 27, 1406 (1962)] or can be prepared by the processes published therein. In the case in which $R^2$ and $R^3$, likewise as defined above, together with the nitrogen atom form a heterocyclic or benzo-fused heterocyclic 5- or 6-membered ring system optionally substituted by a methyl group, the compounds of the general formula (V) are known in some cases [cf. Isv. Akad. Nauk. SSSR, 1422 (1987); J. Org. Chem. 27, 1406 (162); U.S. Pat. Nos. 3,956,333; 3,927,000; 3,855,228] or are new and can then be prepared, for example, by reaction with sulphur tetrafluoride and the corresponding amino acids in solvents, preferably such as hydrofluoric acid.

The compounds of the general formula (IVa) are known in some cases ($R^1$=—$CH_2$—$C_6H_5$; —$CH_2$—$C_6H_{11}$) [cf. J. R. Luly et al., J. Org. Chem. 52, 1487 (1987)] or can be prepared by the methods described therein.

The compounds of the general formula (VI) are also new and can be prepared by the process mentioned under [B].

The compounds of the general formulae (VIII) and (VIIIa) are known or can be prepared by methods known from the literature [cf. EP 402,646].

The compounds of the general formula (IX) are known in some cases [$R^1$=—CH=—$C_6H_5$; —$CH_2$—$C_6H_{11}$) [cf. J. Org. Chem. 50, 5399 (1985); EP 202,577; EP 337,714 or J. Med. Chem. 32, 1371 (1989)] or are new and can be prepared, however, in this case in analogy to the abovementioned published processes, for example by reaction of the appropriate aldehyde with vinylmagnesium bromide in inert solvents, preferably tetrahydrofuran.

The compounds of the general formula (X) are also known in some cases [cf. EP 230,266; EP 189,203; EP 311,012 and J. Med. Chem. 32, 1371 (1989)] or are new (for example $R^1$=—$CH_2C_6H_5$) and can then be prepared in analogous processes.

It has surprisingly been found that the compounds of the general formula (I) have an extremely strong action against retroviruses. This is confirmed by an HIV-specific protease enzyme test.

The results of the examples shown below were determined by the HIV test system described in the following literature references [cf. Hansen, J., Billich, S., Schulze, T., Sukrow, S. and Mölling, K. (1988), EMBO Journal, Vol. 7, No. 6, pp. 1785–1791]: Purified HIV protease was incubated with synthetic peptide which imitated a cleavage site in the Gag precursor protein and represented an in vivo cleavage site of the HIV protease. The resulting cleavage products of the synthetic peptide were analyzed by means of reverse phase high performance liquid chromatography (RP—HPLC). The $IC_{50}$ values given relate to the substance concentration which causes a 50% inhibition of the protease activity under the abovementioned test conditions.

Enzyme assay, HIV-1/HIV-2

TABLE I

| Ex. No. | IC$_{50}$ (RP-HPLC) (M) HIV-1 | HIV-2 |
|---|---|---|
| 12 | 5 × 10$^{-9}$ | 10$^{-9}$ |
| 14 | 10$^{-8}$ | not tested |
| 18 | 5 × 10$^{-9}$ | not tested |
| 19 | 10$^{-8}$ | not tested |
| 22 | 10$^{-9}$ | not tested |
| 24 | 5 × 10$^{-8}$ | not tested |
| 31 | 10$^{-10}$ | not tested |
| 35 | 10$^{-9}$ | not tested |
| 36 | 5 × 10$^{-7}$ | not tested |
| 37 | 5 × 10$^{-9}$ | not tested |
| 43 | 5 × 10$^{-8}$ | not tested |
| 45 | 15$^{-10}$ | not tested |
| 72 | 10$^{-8}$ | not tested |
| 75 | 5 × 10$^{-10}$ | not tested |

The compounds according to the invention additionally showed action in lentivirus-infected cell cultures. This could be shown by the example of the HIV virus.

HIV infection in cell culture

The HIV test was carried out with slight modifications according to the method of Pauwels et al. [cf. Journal of Virological Methods 2Q, (1988), 309-321].

Normal human blood lymphocytes were concentrated by means of Ficoll-Hypaque and stimulated in RPMI 1640, 20% foetal calf serum containing phytohaemaglutinin (90 μg/ml) and interleukin-2 (40 U/ml). For infection with the infectious HIV, PBLs were pelleted and the cell pellet was then suspended in i ml of HIV virus adsorption solution and incubated for 1 hour at 37° C. The virus adsorption solution was centrifuged and the infected cell pellet was taken up in a growth medium such that a concentration of $1 \times 10^5$ cells per ml was established. The cells infected in this way were piperted into the wells of 96-well microtitre plates at a concentration of $1 \times 10^4$ cells/well.

The first vertical row of the microtitre plate contained only growth medium and cells which had not been infected, but had otherwise been treated exactly as described above (cell control). The second vertical row of the microtitre plate contained only HIV-infected cells (virus control) in growth medium. The other wells contained the compounds according to the invention in differing concentrations, starting from the wells of the 3rd vertical row of the microtitre plate, the test substances of which were diluted 10 times in two-fold steps.

The test batches were incubated at 37° C. until the syncytia formation typical of HIV occurred in the untreated virus control (between days 3 and 6 after infection), which was then assessedby microscopy. In the untreated virus control about 20 syncytia resulted under these test conditions while the untreated cell control contained no syncytia.

The IC$_{50}$ values were determined as the concentration of the treated and infected cells at which 50% (about 10 syncytia) of the virus-induced syncytia were suppressed by the treatment with the compound according to the invent ion.

It has now been found that the compounds according to the invention protect HIV-infected cells from virus-induced cell destruction.

TABLE II

| Ex. No. | IC$_{50}$ (μM) [PBL] | [H-9] |
|---|---|---|
| 8 | 5 | — |
| 12 | 0.14 | 0.53 |
| 14 | 1.4 | — |
| 18 | — | 1.1 |
| 20 | 0.5–1 | 2.0 |
| 24 | 2.5 | — |
| 26 | — | 1.5 |
| 37 | — | 2.5 |
| 45 | 5 | — |
| 69 | — | 16 |
| 71 | — | 6.5 |

The compounds according to the invention are useful active substances in human and veterinary medicine for the treatment and prophylaxis of diseases caused by retroviruses.

Examples of indication areas in human medicine which can be mentioned are:
1.) The treatment and prophylaxis of human retrovirus infections.
2.) For the treatment or prophylaxis of diseases (AIDS) caused by HIV I (human immunodeficiency virus; earlier known as HTLV III/LAV) and HIV II and the stages associated with these such as ARC (AIDS-related complex) and LAS (lymphadenopathy syndrome) and the immunodeficiency and encephalopathy caused by this virus.
3.) For the treatment or the prophylaxis of an HTLV-I or HTLV-II infection.
4.) For the treatment or the prophylaxis of the AIDS-carrier state (AIDS-transmitter state).

Examples of indications which can be mentioned in veterinary medicine are:
Infections with
a) Maedi-visna (in sheep and goats)
b) progressive pneumonia virus (PPV) (in sheep and goats)
c) caprine arthritis encephalitis virus (in sheep and goats)
d) Zwoegerziekte virus (in sheep)
e) infectious anaemia virus (of the horse)
f) infections caused by feline leukaemia virus
g) infections caused by feline immunodeficiency virus (FIV)
h) infections caused by simian immunodeficiency virus (SIV)

Preferred areas from the indication area in human medicine are the abovementioned items 2, 3 and 4.

The present invention includes pharmaceutical preparations which, in addition to non-toxic, inert pharmaceutically suitable excipients, contain one or more compounds of the formula (I) or which consist of one or more active substances of the formula (I), and processes for the production of these preparations.

The active substances of the formula (I) should be present in the abovementioned pharmaceutical preparations, preferably in a concentration of about 0.1 to 99.5, preferably from about 0.5 to 95% by weight, of the total mixture.

The abovementioned pharmaceutical preparations can also contain other pharmaceutical active substances apart from the compounds of the formula (I).

The abovementioned pharmaceutical preparations are prepared in a customary manner by known methods, for example by mixing the active substance or substances with the excipient or excipients.

In general, it has proved advantageous both in human and in veterinary medicine to administer the active substance or substances according to the invention in total amounts of about 0.5 to about 500, preferably 1 to 100, mg/kg of body weight every 24 hours, if appropriate in the form of several individual doses, to achieve the desired results. An individual dose contains the active substance or substances preferably in amounts of about 1 to 80, in particular 1 to 30, mg/kg of body weight. However, it may be necessary to depart from the dosages mentioned, in particular depending on the type and the body weight of the subject to be treated, the nature and the severity of the disease, the nature of the preparation and the administration of the medicament and the period or interval within which administration takes place.

Appendix to the experimental section

I. List of the solvent mixtures used for chromatography:
I dichloromethane: methanol
II toluene: ethyl acetate
III acetonitrile: water
IV dichloromethane: methanol: ammonia (9:1:0.1)
V toluene: acetonitrile II. Amino acids In general, the configuration is indicated by placing an L or D before the amino acid abbreviation, in the case of the racemate a D,L-, it being possible for simplification in the case of L-amino acids for indication of the configuration to be suppressed and then for an explicit indication only to take place in the case of the D-form or of the D,L-mixture.

| Ala | L-alanine |
| Arg | L-arginine |
| Asn | L-asparagine |
| Asp | L-aspartic acid |
| Cys | L-cysteine |
| Gln | L-glutamine |
| Glu | L-glutamic acid |
| Gly | L-glycine |
| His | L-histidine |
| Ile | L-isoleucine |
| Leu | L-leucine |
| Lys | L-lysine |
| Met | L-methionine |
| Pro | L-proline |
| Phe | L-phenylalanine |
| Ser | L-serine |
| Thr | L-threonine |
| Trp | L-tryptophan |
| Tyr | L-tyrosine |
| Val | L-valine |

III. Abbreviations

| III. Abbreviations | |
|---|---|
| Z | benzyloxycarbonyl |
| Boc | tert-butoxycarbonyl |
| CMCT | 1-cyclohexyl-3-(2-morpholinoethyl)carbodiimide metho-p-toluenesulfonate |
| DCC | dicyclohexylcarbodiimide |
| DMF | dimethylformamide |
| HOBT | 1-hydroxybenzotriazole |
| Mir | myristoyl |
| Ph | phenyl |
| THF | tetrahydrofuran |
| Cha | cyclohexylalanine |
| MCPBA | m-chloroperbenzoic acid |
| MMPP | magnesium monoperoxyphthalate hexahydrate |
| Aib | 2-amino-2-methylpropionic acid |

Starting Compounds

Example I (S)-2-Amino-1-phenylbut-3-ene hydrochloride

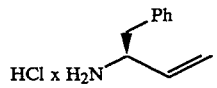

A solution of 5.00 g (20.21 mmol) of (S)-2-(tert-butoxycarbonylamino-1-phenylbut-3-ene [J.R. Luly et al., J. Org. Chem. 52, 1487 (1987)] in 100 ml of a 4 N solution of gaseous hydrogen chloride in anhydrous dioxane was stirred at room temperature for 30 min. 15 ml of toluene were then added and the mixture was concentrated in vacuo. This process was repeated a further two times, then the residue was triturated with a little ether, filtered off with suction and dried in a high vacuum over KOH. 3.69 g (99% of theory) of the title compound were obtained as colourless crystals. $R_f$=0.67, eluent mixture IV MS (DCI, NH$_3$): m/e=148 (M+H$^+$)

Example II (S)-2-Amino-1-cyclohexylbut-3-ene hydrochloride

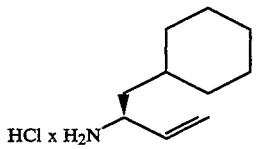

As described for Example I, 3.76 g (99% of theory) of the title compound were obtained as colourless crystals from 5.07 g (20.00mmol) of (S)-2-(tert-butoxycarbonylamino-1-cyclohexylbut-3-ene [J. R. Luly et al., J. Org. Chem. 52, 1487 (1987)]. Melting point: 232°–233° C. $R_f$=0.42 III (9:1) MS (EI, 70 eV) m/e=153 (M)$^+$ Example III (2S) -2-[N-(tert-Butoxycarbonyl-L-valinyl)] amino-1-phenylbut-3-ene

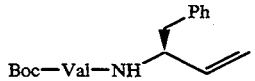

A stirred solution, cooled to 0° C., of 4.81 g (22.13mmol) of N-(tert-butoxycarbonyl)-L-valine and 3.29 g (24.35 mmol) of HOBT in 40 ml of anhydrous dichloromethane was treated with 5.29 g (25.65 mmol) of DCC and stirred for 5 min. A solution of 3.70 g (20.12 mmol) of the compound from Example I and 8.85 ml (80.48 mmol) of N-methylmorpholine in 30 ml of dichloromethane was then added dropwise. The cooling bath was removed and the reaction mixture was stirred at room temperature for 2 h. The end of the reaction was determined by thin layer chromatography. The resulting urea was removed by filtration, the filtrate was concentrated in vacuo and the crude product was purified by chromatography on 450 g of silica gel (dichloromethane: methanol 95:5). 6.07 g (87% of theory) of the title compound were obtained as a colourless foam. R$_f$=0.41, IV MS(DCI, NH$_3$): m/e=347 (M+H)$^+$

Example IV (2S) -2-[(N-(tert-Butoxycarbonyl)-L-valinyl)]amino-1-cyclohexylbut-3-ene

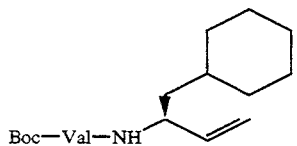

As described for Example III, 4.33 g (65% of theory) of the title compound were obtained as colourless crystals from 3.60 g (19.00 mmol) of the compound from Example II and 4.63 g (21.3 mmol) of Boc—Val—OH. Melting point: 127°–128° C. (Dec.) R$_f$=0.27, II(9:1) MS (DCI, NH$_3$) m/e=353 (M+H)$^+$

Example V (2S) -1-Phenyl-2-(N-L-valinyl)aminobut-3-ene hydrochloride

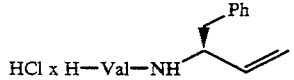

As described for Example I, 4.90 g (99% of theory) of the title compound were obtained as a colourless powder from 6.08 g (17.53 mmol) of the compound from Example III. R$_f$=0.36, I (9:1)

Example VI (2S) -1-Cyclohexyl-2-(N-L-valinyl)aminobut-3-ene hydrochloride

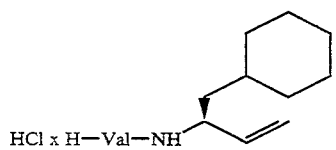

As described for Example I, 3.37 g (95% of theory) of the title compound were obtained as a colourless powder from 4.32 g (12.30 mmol) of the compound from Example IV. Melting point: 169°–170° C. R$_f$=0.48, III(9:1) MS (DCI, NH$_3$) m/e=253 (M+H)$^+$

Example VII (2S) -2-[N-(2S)-3-(tert-Butylsulfonyl)-2-(1-naphthylmethyl) propanoyl]-L-valinyl]amino-1-phenylbut-3-ene

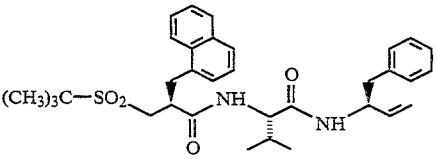

A stirred solution, cooled to 0° C., of 1.50 g (4.47 mmol) of (2S)-3-tert-butylsulfonyl-2-(1-naphthylmethyl)propionic acid [prepared according to H. Bühlmayer et al., J. Med. Chem. 31, 1839 (1988)] and 0.66 g (4.92 mmol) of HOBT in 15 ml of anhydrous dichloromethane was treated with 0.97 g (4.69 mmol) of DCC and stirred for 5 min. A solution of 1.15 g (4.07 mmol) of the compound from Example V and 1.80 ml (16.27 mmol) of N-methylmorpholine in 10 ml of dichloromethane was then added dropwise and the reaction was stirred at room temperature for 1 h. The resulting urea was removed by filtration, the filtrate was concentrated in vacuo and the crude product was purified by chromatography on 270 g of silica gel (dichloromethane: methanol 95:5). 2.01 g (88% of theory) of the title compound were obtained as a colourless foam. R$_f$=0.47, I (95:5) MS (FAB) m/e=563 (M+H)$^+$ As described for Example VII, by coupling the appropriate acids with the amine hydrochlorides (starting materials) the following products (Table I) were obtained:

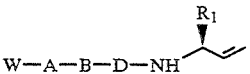

TABLE I

| Example No. | W—A—B—D— | R$^1$ | Yield (%) | MS (FAB) m/e (M+H)$^+$ | R$_f$/eluent ratio | Starting material from Example |
|---|---|---|---|---|---|---|
| VIII | 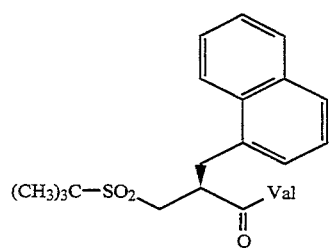 | C$_6$H$_{11}$—CH$_2$ | 76 | 569 | 0.57, I(1:1) | VI |

TABLE I-continued

| Example No. | W—A—B—D— | R¹ | Yield (%) | MS (FAB) m/e (M + H)⁺ | R_f/eluent ratio | Starting material from Example |
|---|---|---|---|---|---|---|
| IX | (CH₃)₃C—SO₂—CH₂—CH(CH₂C₆H₅)—CO—Val | C₆H₅—CH₂ | 92 | 513 | 0.48, I(95:5) | |
| X | (CH₃)₃C—SO₂—CH₂—CH(CH₂C₆H₅)—CO—Val | C₆H₁₁—CH₂ | 75 | 519 | 0.56, II(1:1) | VI |
| XI | CH₃—SO₂—Phe—Val | CH₂—C₆H₅ | 62 | 472 | 0.12, I(95:5) | V |
| XII | CH₃—SO₂—Phe—Val | CH₂—C₆H₁₁ | 58 | 478 | 0.50, II(1:1) | VI |
| XIII | CH₃—C₆H₄—SO₂—Phe—Val | CH₂—C₆H₅ | 29 | 548 | 0.53, I(95:5) | V |
| XIV | CH₃—C₆H₄—SO₂—Phe—Val | CH₂—C₆H₁₁ | 21 | 554 | 0.70, II(1:1) | VI |
| XV | (CH₃)₃C—CH₂—CO—Phe—Val | CH₂—C₆H₅ | 80 | 492 | 0.31, I(95:5) | V |
| XVI | (CH₃)₃C—CH₂—CO—Phe—Val | CH₂—C₆H₁₁ | 57 | 498 | 0.25, I(95:5) | VI |
| XVII | Boc—Phe—Val | CH₂—C₆H₅ | 74 | 494 | 0.44, I(95:5) | V |
| XVIII | Boc—Phe—Val | CH₂—C₆H₁₁ | 62 | 500 | 0.38, I(95:5) | VI |
| XIX | Z—Phe—Val | CH₂—C₆H₅ | 65 | 528 | 0.56, I(95:5) | V |
| XX | Z—Phe—Val | CH₂—C₆H₁₁ | 75 | 534 | 0.25, I(95:5) | VI |
| XXI | Boc—NH—CH(CH₂-cyclohexyl)—CO—Val | CH₂—C₆H₅ | 84 | 500 | 0.43, I(95:5) | V |
| XXII | Boc—NH—CH(CH₂-cyclohexyl)—CO—Val | CH₂—C₆H₁₁ | 70 | 506 | 0.38, I(95:5) | VI |
| XXIII | CH₃(CH₂)₁₂—CO—Phe—Val | CH₂—C₆H₅ | 82 | 604 | 0.34, I(95:5) | V |
| XXIV | quinoline-2-CO—Val | CH₂—C₆H₅ | 54 | 402 | 0.61, I(95:5) | V |
| XXV | quinoline-2-CO—Val | CH₂—C₆H₁₁ | 54 | 408 | 0.21, II(4:1) | VI |
| XXVI | indole-2-CO—Val | CH₂C₆H₅ | 96 | 390 | 0.51, I(95:5) | V |
| XXVII | Boc—Aib | CH₂—C₆H₅ | 52 | 333 | 0.51, I(97:3) | I |

TABLE I-continued

| Example No. | W—A—B—D— | R¹ | Yield (%) | MS (FAB) m/e (M + H)⁺ | $R_f$/eluent ratio | Starting material from Example |
|---|---|---|---|---|---|---|
| XXVIII | Boc—Phe—Gly—Gly | $CH_2$—$C_6H_5$ | 77 | 509 | 0.45, IV | I |
| XXIX | Boc—Ser—Phe | $CH_2$—$C_6H_5$ | 34 | 482 | 0.45, I(9:1) | I |
| XXX | Boc—Asn | $CH_2$—$C_6H_5$ | 38 | 362 | 0.13, I(95:5) | I |
| XXXI | Boc—Ile | $CH_2$—$C_6H_5$ | 64 | 361 | 0.58, I(97:3) | I |
| XXXII | 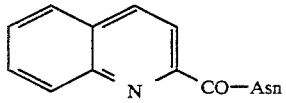 | $CH_2$—$C_6H_5$ | 39 | 417 | 0.26, I(95:5) | XXXVII |
| XXXIII | 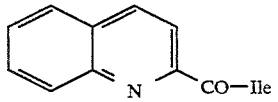 | $CH_2$—$C_6H_5$ | 90 | 416 | 0.28, II(4:1) | XXXVIII |
| XXXIV | 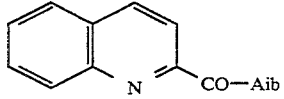 | $CH_2$—$C_6H_5$ | 70 | 388 | 0.48, II(7:3) | XXXIX |
| XXXV | 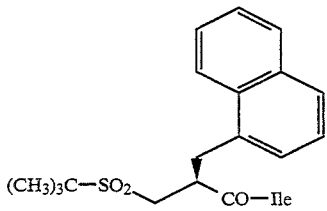 | $CH_2$—$C_6H_5$ | 72 | 576 | 0.18, II(7:3) | XXXVIII |
| XXXVI | 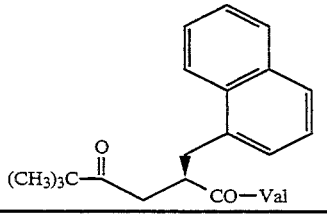 | $CH_2$—$C_6H_5$ | 78 | 527 | 0.39, II(7:3) | V |

As described for Example I, the following products (Table 2) were obtained by removal of the tertbutoxycarbonyl protective group from the corresponding starting materials:

TABLE 2

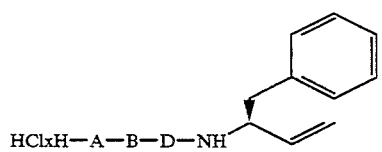

| Example No. | H—A—B—D— | Yield (%) | MS (FAB) m/e (M + H)⁺ | $R_f$/eluent ratio | Starting material from Example |
|---|---|---|---|---|---|
| XXXVII | H—Asn | 92 | 262 | 0.06, I(9:1) | XXX |
| XXXVIII | H—Ile | 91 | 261 | 0.58, I(95:5) | XXXI |
| XXXIX | H—Aib | 88 | 233 | 0.35, I(97:3) | XXVII |

Example XL

2-{1-[N-[(tert-Butylacetyl)-L-phenylalanyl]-L-valinyl]amino-2-phenyl-(1S)-ethyl}oxirane

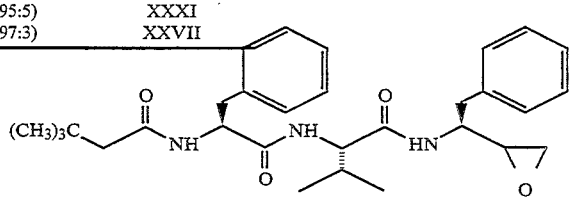

A stirred suspension, cooled to 0° C., of 250 mg (0.60 mmol) of the compound from Example XV in 3 ml of dichloromethane was treated in portions with 259 mg (1.20 mmol −2 equiv.) of m-chloroperbenzoic acid (80% strenth) (MCPBA) and stirred at this temperature for 2 h. A further 130 mg (0.60mmol—1 equiv.) of MCPBA were then added and the mixture was additionally stirred at room temperature for 1 h. 10 ml of ethyl acetate were then added and the reaction mixture was stirred into 20 ml of a 10% strength $Na_2SO_3$ solution. The organic phase was separated off, washed 3 times with 10 ml of $NaHCO_3$ solution and dried over $MgSO_4$. After evaporation of the solvent in vacuo and titration of the residue with a little ether/pentane, 253 mg (83% of theory) of the title compound were obtained as a colourless powder. Melting point: 168° C. (dec.) $R_f$=0.26, I(97:3) MS(FAB) m/e=508 (M+H)+

Example XLI (2S) -{1-[N-[(2S) -Benzyl-3-(tert-butylsulfonyl)-propanoyl]L-valinyl]amino-2-phenyl-(1S)-ethyl}oxirane A suspension of 345 mg (0.67 mmol) of the compound from Example IX, 8 mg (5 mol%) of benzyltriethylammonium chloride and 668 mg (1.35 mmol) of magnesium monoperoxyphthalate hexahydrate (MMPP) in 3 ml of chloroform was adjusted to pH 5 by addition of 1 N NaOH solution and heated to reflux for 16 h, a pH of about 5 being maintained byaddition of small amounts of 1 N NaOH. After cooling, the reaction mixture was filtered with suction and the filtrate was washed with 10 ml of water, 10 ml of 10% strength $NaSO_3$ solution and 10 ml of dilute $NaHCO_3$ solution and dried over magnesium sulphate. After evaporation of the solvent in vacuo and chromatography of the residue on 15 g of silica gel (toluene: ethyl acetate 1:1), 131 mg (37% of theory) of the title compound were obtained as a colourless hard foam. $R_f$=0.21, II(1:1) MS(FAB) m/e=529 (M+H)+ HPLC: Mixture of the diastereomeric epoxides (1S):(1R)=16:1

As described for Example XL, the following epoxides were obtained (Table 3):

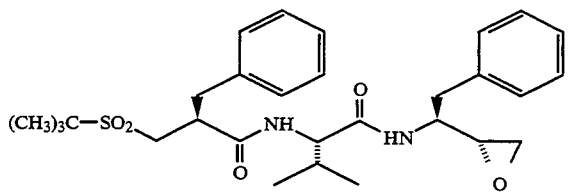

TABLE 3

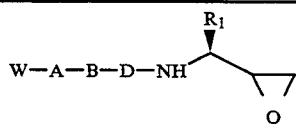

| Example No. | W—A—B—D— | R¹ | Yield (%) | MS(FAB) m/e (M + H)+ | $R_f$/eluent ratio | Starting material from Example |
|---|---|---|---|---|---|---|
| XLII | Z—Phe—Val | $CH_2$—$C_6H_5$ | 81 | 544 | 0.39, I(95:5) | XIX |
| XLIII | Boc—Cha—Val | $CH_2$—$C_6H_5$ | 47 | 516 | 0.53, I(95:5) | XXI |
| XLIV | (CH₃)₃C—SO₂—CH(CH₂-1-naphthyl)—CO—Val | $CH_2$—$C_6H_5$ | 4 | 579 | 0.16, II(4:6) | VII |
| XLV | (CH₃)₃C—SO₂—CH(CH₂-1-naphthyl)—CO—Val | $CH_2$—$C_6H_5$ | 38 | 579 | 0.12, II(4:6) | VII |
| XLVI | (CH₃)₃C—SO₂—CH(C₆H₅)—CO—Val | $CH_2$—$C_6H_5$ | 43 | 529 | 0.21, II(1:1) | IX |
| XLVII | $CH_3$—$SO_2$—Phe—Val | $CH_2$—$C_6H_5$ | 10 | 488 | 0.22, II(1:1) | XI |
| XLVIII | $CH_3$—$SO_2$—Phe—Val | $CH_2$—$C_6H_5$ | 39 | 488 | 0.15, II(1:1) | XI |
| XLIX | Boc—Phe—Val | $CH_2$—$C_6H_5$ | 46 | 510 | 0.05, I(97:3) | XVII |

TABLE 3-continued $$W-A-B-D-NH-\overset{R_1}{\underset{}{C}}H-\underset{O}{\triangle}$$

| Example No. | W—A—B—D— | R¹ | Yield (%) | MS(FAB) m/e (M + H)⁺ | R$_f$/eluent ratio | Starting material from Example |
|---|---|---|---|---|---|---|
| L | quinolin-2-yl-CO—Val | CH$_2$—C$_6$H$_5$ | 66 | 418 | 0.25, II(7:3) | XXIV |
| LI | quinolin-2-yl N-oxide-CO—Val | CH$_2$—C$_6$H$_5$ | 22 | 418 | 0.12, II(7:3) | |
| LII | CH$_3$(CH$_2$)$_{12}$—CO—Phe—Val | CH$_2$—C$_6$H$_5$ | 55 | 620 | 0.33, I(97:3) | XXIII |
| LIII | (CH$_3$)$_3$C—SO$_2$—CH$_2$—CH(CH$_2$Ph)—CO—Val | CH$_2$—C$_6$H$_{11}$ | 54 | 535 | 0.12, I(95:5) | X |
| LIV | (CH$_3$)$_3$C—SO$_2$—CH$_2$—CH(CH$_2$-naphthyl)—CO—Val | CH$_2$—C$_6$H$_{11}$ | 53 | 585 | 0.28, I(97:3) | VIII |
| LV | Boc—Phe—Val | CH$_2$—C$_6$H$_{11}$ | 51 | 516 | 0.11, I(97:3) | XVIII |
| LVI | CH$_3$—SO$_2$—Phe—Val | CH$_2$—C$_6$H$_{11}$ | 55 | 494 | 0.13, I(97:3) | XII |
| LVII | (CH$_3$)$_3$C—CH$_2$—CO—Phe—Val | CH$_2$—C$_6$H$_{11}$ | 48 | 514 | 0.12, I(97:3) | XVI |
| LVIII | Boc—Cha—Val | CH$_2$—C$_6$H$_{11}$ | 55 | 522 | 0.19, I(97:3) | XXII |
| LIX | Z—Phe—Val | CH$_2$—C$_6$H$_{11}$ | 61 | 550 | 0.34, II(6:4) | XX |
| LX | Z—Phe—Val | CH$_2$—C$_6$H$_{11}$ | 8 | 550 | 0.14, II(6:4) | XX |
| LXI | Boc—Ser—Phe | CH$_2$—C$_6$H$_5$ | 38 | 500 | 0.12, I(9:1) | XXIX |
| LXII | Boc—Phe—Gly—Gly | CH$_2$—C$_6$H$_5$ | 49 | 525 | 0.41, I(9:1) | XXVIII |
| LXIII | quinolin-2-yl-CO—Asn | CH$_2$—C$_6$H$_5$ | 17 | 433 | 0.11, I(95:5) | XXXII |
| LXIV | quinolin-2-yl N-oxide-CO—Ile | CH$_2$—C$_6$H$_5$ | 33 | 448 | 0.16, II(3:2) | XXXIII |
| LXV | quinolin-2-yl N-oxide-CO—Aib | CH$_2$—C$_6$H$_5$ | 68 | 420 | 0.13, II(3:2) | XXXIV |

TABLE 3-continued $$W-A-B-D-NH-\overset{R_1}{\underset{\triangle O}{C}}$$

| Example No. | W—A—B—D— | R¹ | Yield (%) | MS(FAB) m/e (M + H)+ | R_f/eluent ratio | Starting material from Example |
|---|---|---|---|---|---|---|
| LXVI | (CH₃)₃C—SO₂—CH₂—CH(CO—Ile)—CH₂-(1-naphthyl) | $CH_2-C_6H_5$ | 89 | 593 | 0.15, II(3:2) | XXXV |
| LXVII | (CH₃)₃C—CO—CH₂—CH(CO—Val)—CH₂-(1-naphthyl) | $CH_2-C_6H_5$ | 21 | 543 | 0.26, II(7:3) | XXXVI |
| LXVIII | (CH₃)₃C—CO—CH₂—CH(CO—Val)—CH₂-(1-naphthyl) | $CH_2-C_6H_5$ | 22 | 543 | 0.16, II(7:3) | XXXVII |

Example LXIX

2-{(1R, 2S)-3-[N-(tert-Butoxycarbonyl)amino ]-1-hydroxy-3-phenylpropyl}oxirane

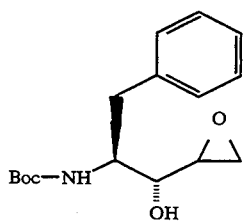

A stirred solution, cooled to 0° C., of 2.77 g (18.0 mmol) of (3S, 4S)-4-[N-(tert-butoxycarbonyl)amino]-3-hydroxy-5-phenylpentene [cf. G. J. Hansen et al., J. Org. Chem. 50, 5399 (1985)] in 28 ml of dichloromethane was treated in portions with 5.18 g (30 mmol—3 equiv.) of m-chloroperbenzoic acid (80% strength) (MCPBA) and stirred at 0° C. for 2 h and at room temperature for 1 h. 50 ml of ethyl acetate were then added and the reaction mixture was stirred into 100 ml of a 20% strength Na₂SO₃ solution. The organic phase was separated off, washed 3 times with 50 ml of 20% strength Na₂CO₃ solution and dried over MgSO₄. After evaporation of the solvent in vacuo and chromatography of the residue on 110 g of silica gel (toluene: ethyl acetate 4:1), 1.87 g (64% of theory) of title compound were obtained as colourless crystals. Melting point: 102° C. R_f—0.21, II(7:3) MS (FAB): m/e=294(M+H)+

Example LXX

2-{(1S, 2S)-2-[N-(tert-Butoxycarbonyl)amino]-1-hydroxy-3phenylpropyl}oxirane

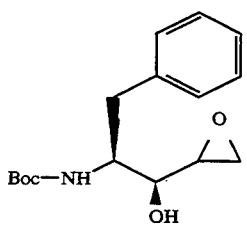

As described for Example LXIX, 2.50 g (85% of theory) of the title compound were obtained as colourless crystals from 2.77 g (10 mmol) of (3S, 4S)-4-[N-(tertbutoxycarbonyl)amino]-3-hydroxy-5-phenylpentene[cf. G. J. Hansen et al., J. Org. Chem. 50, 5399 (1985)] and 6.91 g (40 mmol) of MCPBA after 1 h at 0° C. and 3.5 h at room temperature. Melting point: 118° C. R_f=0.20, II(7:3) MS (DCI, NH₃): m/e=294 (M+H)+

Example LXXI 2-(Trifluoromethyl)-5-methylpyrrolidine

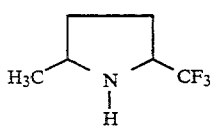

100 g (0.5 mmol) of 6,6,6-Trifluoro-5-nitrohexan-2-one were hydrogenated in 300 ml of methanol on 10 g of Raney-Nickel at 80° C. for 8 hours in a 0.7 l capacity V4A stirred autoclave. The hydrogen partial pressure was 80 bar; 90% of the theoretical amount of hydrogen was absorbed. For working up, the catalyst was filtered off and additionally washed with a little methanol. The methanolic solution was rendered acidic with 100 ml of concentrated hydrochloric acid and concentrated to dryness under reduced pressure. 59 g (0.34 mol) of 2-(trifluoromethyl)-5-methyl-pyrrolidine hydrochloride (67% of theory) resulted. 2-(Trifluoromethyl)-5-methylpyrrolidine was obtained from the hydrochloride by addition of an equimolar amount of sodium hydroxide solution, extraction with diethyl ether, drying over sodium sulphate and subsequent distillative removal of the solvent through a 30 cm long Vigreux column (B.p.$_{1013}$:118°-120° C.). $^{19}$F—NMR: $\delta = +1.0$ ppm (d, $J_{H-F}=7$ Hz) (against external CF$_3$COOH).

Example LXXII 2-(Trifluoromethyl)piperidine a) Racemic (process improvement; M. S. Raasch, J.O.C. 27, 1406 (1972))

38.7 g (0.3 mol) of D,L-piperidine-2-carboxylic acid were reacted in 60 ml of anhydrousHF and 100 g (0.925 mol) of SF$_4$ for 8 h at 120° C. in a V4A stirred vessel (0.3 l). The HF and excess SF$_4$ were then stripped off in vacuo (100 mbar) and the residue was taken up in ice. After filtration, the filtrate was adjusted in a pH of 12 with 40% strength NaOH and filtered again, and the aqueous phase was extracted 4 tLmes with 250 ml of Et$_2$O. After drying over Na$_2$SO$_4$, the Et$_2$O was removed on a rotary evaporator at ND and the residue (crude: 59 g) was distilled at normal pressure. B.p.$_{1013}$ (main fraction): 121°-123° C. Yield: 36 g (0.235 mol) (78.4% of theory) $^{19}$F—NMR: $\delta = +0.45$ ppm (d, $J_{HF}=7$ Hz) (against external CF$_3$COOH).

b) Optically active (starting from L-piperidine-2-carboxylic acid)

5 g (0,039 mol) of L-piperidine-2-carboxylic acid were reacted analogously with 25 g (0.231 mol) of SF$_4$ in 30 ml of HF. After working up, 5.8 g of crude product were obtained which were fractionated by means of a microdistillation apparatus. B.p.$_{1013}$ (main fraction: 120°-122° C.) Yield: 3.8 g (0. 025 mol) (64.1% of theory)

Example LXXIII 2-(Trifluoromethyl)-decahydroquinoline 15 g (0.076 mol) of 2-(Trifluoromethyl)quinoline [prepared from quinoline-2-carboxylic acid according to M. S. Raasch, J. Org. Chem. 27, 1406 (1962)] were hydrogenated in 100 ml of tetrahydrofuran on 2.5 g of ruthenium on alumina (about 10% RU content) at 180° C. for 8 h at an H$_2$ pressure of 80-100 bar in a 0.3 l V4A autoclave. After filtration, the THF was stripped off and the crude product was fractionated in a water pump vacuum by means of a microdistillation apparatus. B.p.$_{16}$ (main fraction): 88° C. Yield: 12.5 g (0.061 mol) (80% of theory) The product was obtained as a diastereomer mixture. $^{19}$F—NMR: $\delta = +0.65$ ppm(d, $J_{H-F}=7.1$ Hz)(according to integral about 88%) $^{19}$F—NMR: $\delta = +0.90$ ppm(d, $J_{H-F}=7.1$ Hz)(according to integral about 12%) (against external CF$_3$COOH).

Example LXXIV 1-(Trifluoromethyl)decahydroisoquinoline 20 g (0,101 mol) of 1-(Trifluoromethyl)-3,4-dihydroisoquinoline [prepared from N-(phenethyl)trifluoroacetamide analogously to U.S. Pat. No. 3,956,333 (11.5.76; Sterling Drug Inc.)] were hydrogenated in 100 ml of tetrahydrofuran on 5 g of ruthenium on alumina (about 10% Ru content) at 150° C. for 8 h at an H2 pressure of 100 bar in a 0.3 l V4A autoclave. After filtration, the THF was stripped off and the crude product was fractionareal in a water pump vacuum by means of a microdistillation apparatus. B.p.$_{16}$ (main fraction): 94°-96° C. Yield: 19 g (0.092 mol) (91% of theory) The product was obtained as a diastereomer mixture. $^{19}$F—NMR: $\delta = +5.9$ ppm(d, $J_{H-F}=8.5$ Hz)(according to integral about 99%) $^{19}$F—NMR: $\delta = +14.2$ ppm(d, $J_{H-F}=8.5$ Hz) (according to integral <1%) (against external CF$_3$COOH).

Example LXXV 3-(Trifluoromethyl)decahydroisoquinoline

Variant A 18 g (0.098 mol) of decahydroisoquinoline-3-carboxylic acid [prepared from 1,2,3,4-tetrahydroisoquinoline-3-carboxylic acid hydrochloride by catalytic hydrogenation] were reacted with 35 g (0.324 mol) of SF$_4$ in 50 ml of anhydrous EF at 8 h at 120° C. in a V4A stirred vessel (0.3l). The HF and excess SF4 were then stripped off in vacuo (100 mbar) and the residue was taken up in ice. After filtration, a pH of 12 was established with 40% strength NaOH, the mixture was filtered again and the aqueous phase was extracted 4 times with 250 ml of Et$_2$O. After drying over Na$_2$SO$_4$, the Et$_2$O was stripped off and the residue (crude: 9.5 g) was fractionated in a water pump vacuum by means of a microdistillation apparatus. B.p.$_{16}$ (main fraction): 89°-94° C. Yield: 4.8 g (0.023 mol) (23.5% of theory) The product was obtained as a diastereomer mixture. $^{19}$F—NMR: $\delta = -1.1$ ppm(d, $J_{H-F}=7$ Hz)(according to integral about 94%) $^{19}$F—NMR: $\delta = -1.3$ ppm (d, $J_{H-F}=7$ Hz) (according to integral about 6%) (against external CF$_3$COOH).

Variant B 20 g (0.101 mol) of 3-(Trifluoromethyl)-3,4-dihydroisoquinoline [prepared from N-(1,1,1-trifluoro-3-phenyl-2propyl)formamide analogously to U.S. Pat. No. 3,956,333 (11.5.76; Sterling Drug Inc.)] were hydrogenated in 100 ml of tetrahydrofuran on 5 g of rutheniumon alumina (about 10% Ru content) at 150°-180° C. for 8 h at an H$_2$ pressure of 90-110 bar in a 0.3 l V4A autoclave. After filtration, the THF was stripped off and the crude product was fractionated in a water pump vacuum by means of a microdistillation apparatus. Main fraction: 93°-94° C. Yields 18.5 g (0.090 mol) (88% of theory) The product was obtained as a diastereomer mixture.

Example LXXVI (3S) - 3- (N-Benzyloxycarbonyl) amino-1-chloro-4-phenylbutan-2 -one

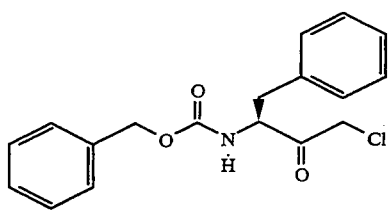

A solution of 40 g of N-Benzyloxycarbonyl-L-phenylalanine (133mmol) in 600 ml of abs. THF is treated with 23 ml of abs. triethylamine and cooled to −40° C. under argon. 22 ml of isobutyl chloroformate are slowly added dropwise with stirring to this solution and it is allowed to react for 30 minutes. The mixture is then freed from the precipitated triethylammonium hydrochloride with cooling by means of an inverted frit and added dropwise to a solution, cooled to −30° C., of 220 mmol of diazomethane in ethanol-free abs. diethyl ether. After 30 minutes the formation of the diazoketone is complete. A 1 molar solution of anhydrous HCl in diethyl ether is slowly added dropwise to this solution until an acidic reaction persists. After completion of the addition, the source of cooling is removed and the mixture is additionally stirred for a further 2 hours. For working up, precipitated salts are filtered off and the liltrate is concentrated. The product obtained in near-lyquantitative yield is sufficiently pure for further reaction (>90%). $R_f$=0.66 (toluene/acetone 6:1).

Example LXXVII (2S,3S)-3-(N-Benzyloxycarbonyl)amino-1-chloro-2-hydroxy-4-phenylbutane

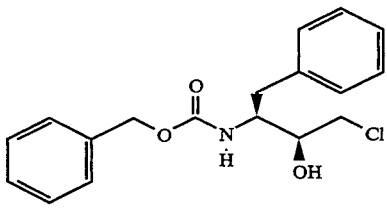

2.1 g of sodium borohydride are added in portions at 0° C. to a solution of 47 g of the compound from Example LXXVI in 500 ml of methanol and the mixture is additionally stirred for a further 15 minutes. For working up, the mixture is adjusted to pH 6 with 2 N HCl and concentrated. The residue obtained is taken up in 200 ml of dichloromethane and washed twice with water. The organic phase is dried and concentrated. The syrupy residue is crystallised from ligroin/acetone 4:1. After recrystallising twice, 20 g of pure (2S)-diastereomer are obtained. The combined mother liquors are crystallised again and after recrystallisation yield a further 5.8 g of pure (2S)-diastereomer. The (2R)-diastereomer does not crystallise under these conditions. Yield [(2S)diastereomer]: 25.8 g (55% of theory) $R_f$=0.37 (toluene/ethanol 10:1)

Example LXXVIII (2R)-[1-(N-Benzyloxycarbonyl)amino-2-phenyl-(1S)ethyl]oxirane

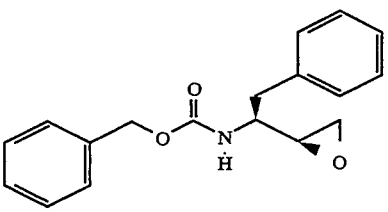

10 g of KOH are added to a solution of 16 g of the compound of Example LXXVII in 600 ml of methanol and the mixture is stirred at room temperature for 30 minutes.

For working up, it is neutralised with glacial acetic acid and concentrated. The residue is taken up in dichloromethane and washed twice with water. The organic phase is dried and concentrated. Yield: 14.6 (92% of theory) $R_f$=0.6 (toluene/ethanol 10:1)

Preparation Examples

Example 1

1-[(2S and 2R, 3S)-3-[(N-tert-Butoxycarbonyl)amino]-2-hydroxy-4-phenylbutyl]-(2S)-2-(trifluoro-methyl) pyrrolidine

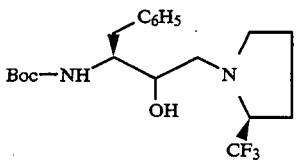

A solution of 4.00 g (15.18 mmol) of (1S)-[1-[1-(tert-butoxycarbonyl)amino]-2-phenyl-(1S,R)ethyl]oxirane [cf. J. R. Luly et al., J. Org. Chem. 52, 487 (1987)] and 2.56 g (18.2mmol) of (2S)-2-(trifluoromethyl)pyrrolidine [G. V. Shustov et al., Isvest. Akad. Nauk. SSSR, 1422 (1987); engl.] in 4 ml of propanol was stirred in a pressure vessel at 110° C. for 2 h. After cooling, the reaction mixture was concentrated in vacuo and, after preliminary purification on 100 g of silica gel, separated by chromatography on 600 g of silica gel (toluene:ethyl acetate 9:1). 3.09 g (51% of theory) of the non-polar diastereomer mixture were obtained as waxy crystals. Melting point: 72° C. $R_f$=0.27, II(9:1) MS (DCI, NH3): m/e=403 (M+H)+ In addition, 1.10 g (18% of theory) of the polar diastereomer were obtained as a powder. Melting point: 98°–100° C. $R_f$=0.10, II(9:1) MS (DCI, NH3): m/e=403 (M+H)+.

Example 2

1-[(2S, 3S)-3-Amino-2-hydroxy-4-phenyl-butyl ]-(2S)-2-(trifluoromethyl)-pyrrolidine dihydrochloride

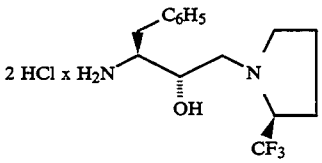

A solution of 3.09 g (7.66 mmol) of the non-polar diastereomer from Example 1 in 30 ml of a 4 N solution of gaseous hydrogen chloride in anhydrous dioxane was stirred at 0° C. for 30 min. 15 ml of toluene was then added and the mixture was concentrated in vacuo. This process was repeated a further 2 times, then the residue was tritrated with ether, filtered off with suction and dried over KOH in a high vacuum. 2.84 g (99% of theory) of the title compound were obtained as a colourless powder. R_f=0.42, III(9:1) MS (FAB): m/e=303 (M+H)+, 337 (M+Na)+, 359 (M+2Na—H)+

Example 3

1-[(2R, 3S)-3-Amino-2-hydroxy-4-phenyl-butyl]-(2S)-2(trifluoromethyl)-pyrrolidine dihydrochloride

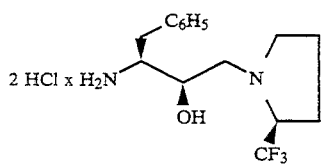

As described for Example 2, 1.03 g (96% of theory) of the polar amine dihydrochloride were obtained as a powder from 1.15 g (2.84 mmol) of the polar diastereomer from Example 2. R_f=0.40, III(9:1) MS (DCI, NH_3): m/e=303 (M+H)+

Example 4

1-[(2S, 3S)-3-[(N-tert-Butoxycarbonyl-L-valinyl)amino]-2-hydroxy-4-phenylbutyl]-(2S)-2-(trifluoromethyl)pyrrolidine

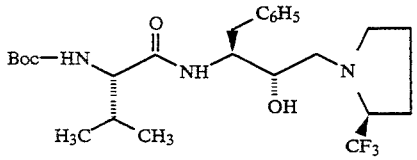

A stirred solution, cooled to 0° C., of 4.81 g (22.13 mmol) of N-(tert-butoxycarbonyl)-L-valine and 3.29 g (24.35 mmol) of HOBT in 40 ml of anhydrous dichloromethane was treated with 5.29 g (25.65 mmol) of DCC and stirred for 5 min. A solution of 3.70 g (20.12 mmol) of the compound from Example 2 and 8.85 ml (80.48 mmol) of N-methylmorpholine in 30 l of dichloromethane was then added dropwise. The cooling bath was removed and the reaction solution was stirred at room temperature for 2 h. The end of the reaction was determined by thin layer chromatography. The resulting urea was removed by filtration, the filtrate was concentrated in vacuo, and the crude product was purified by chromatography on 400 g of silica gel (dichloromethane: methanol). 6.89 g (68% of theory) of the title compound were obtained as a colourless foam. R_f= MS (DCI, NH_3): m/e=503 (M+H)+

EXAMPLE 5

1-[(2R, 3S)-3-[(N-tert-Butoxycarbonyl-L-valinyl)amino]-2-hydroxy-4-phenylbutyl]-(2S)-2-(trifluoromethyl)pyrrolidine

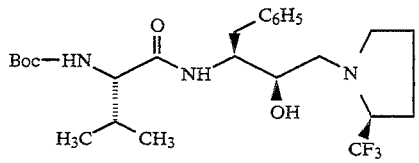

As described for Example 4, 541 mg (59% of theory) of the polar diastereomer were obtained as a foam from 555 mg (1.82 mmol) of the compound from Example 3. MS (FAB): m/e=503 (M+H)+

Example 6

1-[(2R, 3S)-3-[(N-tert-Butoxycarbonyl-L-asparaginyl) amino]-2-hydroxy-4-phenylbutyl]-(2S)-2(trifluoromethyl)-pyrrolidine

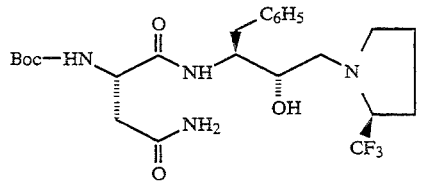

A stirred solution of 731 mg (3.12 mmol) of N-(tert-butoxycarbonyl)-L-asparagine in 6 ml of anhydrous DMF was treated at 0° C. with 530 mg (3.44 mmol) of HOBT and 1.39 g (3.28 mmol) of CMTC. A solution of 1,114 mg (2.84 mmol) of the compound from Example 3 and 1.6 ml (14.20 retool) of N-methylmorpholine in 8 ml of DMF was then added. The cooling bath was removed and the mixture was stirred at room temperature for 3 h. It was then concentrated in vacuo and the residue was partitioned between 40 ml of ethyl acetate and 40 ml of water. The water phase was extracted with 10 ml of ethyl acetate, and the combined extracts were washed with 50 ml of water and dried over MgSO_4. After evaporation of the solvent in vacuo and chromatography of the crude product on 200 g of silica gel (dichloromethane:methanol 9:1), 1.42 g (89% of theory) of the title compound were obtained as crystals. Melting points: 104° C. R_f=0.15, I(9:1) MS(FAB): m/e=517 (M+H)+

Example 7

1-[(2S, 3S)-3-[(N-tert-Butoxycarbonyl-L-asparaginyl)amino ]-2-hydroxy-4-phenylbutyl]-(2S)-2-(trifluoromethyl)-pyrrolidine

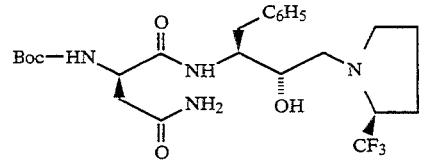

As described for Example 6, 194 mg of the title compound were obtained as crystals from 346 mg (1.49 mmol) of N-(tert-butoxycarbonyl)-L-asparagine and 615 mg (1.64 mmol) of the non-polar diastereomer from Example 2 after chromatography of the crude product on 75 g of silica gel (dichloromethane: methanol 9:1). Melting point: 161° C. $R_f$=0.42, I(9:1) MS(FAB): m/e=517 (M+H)+

As described for Example LXIV, the following products (Table 4) were obtained from the corresponding oxiranes (starting material) and the corresponding trifluoromethyl bases $HNR_2$—$CH(CF_3)R^3$:

(The allocation of the stereochemistry of the OH group to the polar or non-polar diastereomers of Examples 1-7 was carried out tentatively.)

TABLE 4

W—A—B—D—NH—CH(CH$_2$C$_6$H$_5$)—CH(OH)—L

| Example No. | W—A—B—D— | L | Yield (%) | MS(FAB) m/e (M + H)+ | $R_f$/eluent ratio | Starting material from Example |
|---|---|---|---|---|---|---|
| 8 | quinolin-2-yl-CO—Val— | —N(pyrrolidinyl-CF$_3$) | 33 | 557 | 0.26, II(7:3) | L |
| 9 | quinoline N-oxide-2-yl-CO—Val— | —N(pyrrolidinyl-CF$_3$) | 53 | 573 | 0.18, II(7:3) | LI |
| 10 | quinoline N-oxide-2-yl-CO—Ile— | —N(pyrrolidinyl-CF$_3$) | 53 | 587 | 0.33, II(3:2) | LXIV |
| 11 | quinoline N-oxide-2-yl-CO—Aib— | —N(pyrrolidinyl-CF$_3$) | 68 | 559 | 0.27, I(97:3) | LXV |
| 12 | (CH$_3$)$_3$—C—SO$_2$—CH$_2$—CH(CH$_2$-naphth-1-yl)—CO—Val— | —N(pyrrolidinyl-CF$_3$) | 55 | 718 | 0.30, I(97:3) | XLV |
| 13 | (CH$_3$)$_3$—C—SO$_2$—CH$_2$—CH(CH$_2$-naphth-1-yl)—CO—Val— | —N(pyrrolidinyl-CF$_3$) | 54 | 718 (144) | 0.14, I(97:3) | XLIV |

TABLE 4-continued

W—A—B—D—NH—CH(CH₂C₆H₅)—CH(OH)—CH₂—L

| Example No. | W—A—B—D— | L | Yield (%) | MS(FAB) m/e (M + H)⁺ | R$_f$/eluent ratio | Starting material from Example |
|---|---|---|---|---|---|---|
| 14 | (CH₃)₃C—SO₂—CH₂—CH(CO—Ile—)— (naphthyl) | —N(pyrrolidinyl-CF₃) | 34 | 732 | 0.24, II(2:3) | LXVIII |
| 15 | Boc—Phe—Gly—Gly | —N(pyrrolidinyl-CF₃) | 87 | 664 | 0.16, I(95:5) Melting point: 172° C. | LXII |
| 16 | CH₃(CH₂)₁₂CO—Phe—Val | —N(pyrrolidinyl-CF₃) | 61 | 759 | 0.27, II(3:2) Melting point: 109° C. | LII |
| 17 | Boc—Phe—Val | —N(pyrrolidinyl-CF₃) | 32 | 649 | 0.14, II(7:3) Melting point: 155° C. | XLIX |
| 18 | (CH₃)₃C—SO₂—CH₂—CH(CO—Val—)— (naphthyl) | —N(piperidinyl-CF₃) | 36 | 732 | 0.12, I(97:3) | XLV |
| 19 | (CH₃)₃C—SO₂—CH₂—CH(CO—Val—)— (naphthyl) | HN—CH(iPr)(CF₃) | 37 | 720 | 0.25, II(1:1) | XLV |
| 20 | (CH₃)₃C—SO₂—CH₂—CH(CO—Val—)— (naphthyl) | —N(2,5-dimethyl/CF₃-pyrrolidinyl) | 16 | 732 | 0.21, II(3:2) non-polar | XLV |

TABLE 4-continued $$\text{W—A—B—D—NH}\underset{\underset{\text{OH}}{|}}{\overset{\overset{C_6H_5}{|}}{C}}\text{—L}$$

| Example No. | W—A—B—D— | L | Yield (%) | MS(FAB) m/e (M + H)+ | $R_f$/eluent ratio | Starting material from Example |
|---|---|---|---|---|---|---|
| 21 | (CH₃)₃C—SO₂—...—CO—Val— (naphthyl) | pyrrolidine with CH₃ and CF₃ | 22 | 732 | 0.19, II(3:1) polar | XLV |
| 22 | (CH₃)₃C—SO₂—...—CO—Val— (naphthyl) | tetrahydroisoquinoline-CF₃ | 47 | 780 | 0.20, II(3:2) polar | XLV |
| 23 | (CH₃)₃C—SO₂—...—CO—Val— (naphthyl) | tetrahydroisoquinoline-CF₃ | 49 | 780 | 0.29, II(3:2) non-polar | XLIV |
| 24 | (CH₃)₃C—SO₂—...—CO—Val— (naphthyl) | decahydroisoquinoline-CF₃ | 22 | 786 | 0.36, II(3:2) | XLV |
| 25 | (CH₃)₃C—SO₂—...—CO—Val— (naphthyl) | decahydroisoquinoline-CF₃ | 18 | 786 | 0.24, II(3:2) | XLV |
| 26 | (CH₃)₃C—SO₂—...—CO—Val— (naphthyl) | decahydroisoquinoline-CF₃ | 14 | 786 | 0.19, II(7:3) | XLV |

TABLE 4-continued

W—A—B—D—NH—CH(C₆H₅)—CH(OH)—CH₂—L

| Example No. | W—A—B—D— | L | Yield (%) | MS(FAB) m/e (M + H)⁺ | $R_f$/eluent ratio | Starting material from Example |
|---|---|---|---|---|---|---|
| 27 | (CH₃)₃C—SO₂—CH(CH₂-naphthyl)—CO—Val— | decahydroisoquinolinyl-CF₃ | 10 | 786 | 0.14, II(7:3) | XLV |
| 28 | (CH₃)₃C—CO—CH(CH₂-naphthyl)—CO—Val— | 2-(CF₃)-piperidinyl | 51 | 682 | 0.21, II(7:3) | LXVII |
| 29 | (CH₃)₃C—CO—CH(CH₂-naphthyl)—CO—Val— | 2-(CF₃)-piperidinyl | 58 | 682 | 0.29, II(7:3) | LXVIII |

Example 30

1-{(2S, 3S)-3-[(N-tert-Butoxycarbonyl-L-phenylalaninyl)-L-valinyl)amino]-4-cyclohexyl-2-hydroxybutyl}-(2S)-2(trifluoromethyl)-pyrrolidine

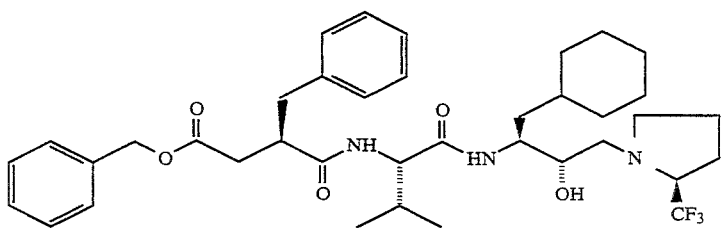

A solution of 135 mg (0.25 mmol) of the compound from Example LIX and 70 mg (0.50 mmol) of (2S)-2-(trifluoromethyl)-pyrrolidine [cf. G. V. Shustov et al., Isvest. Akad. Nauk. SSSR, 1422 (1987) engl.] in 0.5 ml of n-propanol was stirred in a pressure vessel at 110° C. for 5 h. After cooling, the reaction mixture was concentrated in vacuo and chromatographed on 10 g of silica gel (toluene: ethyl acetate 7:3). After triturating with n-pentane, 129 mg (76% of theory) of the title compound were obtained as crystals. Melting point: 109° C. $R_f$=0.34, II(7:3) MS(FAB): m/e=689 (M+H)⁺

As described for Example 2, the following products (Table 5) were obtained by removal of the tertbutoxycarbonyl protective group from the corresponding starting materials:

TABLE 5

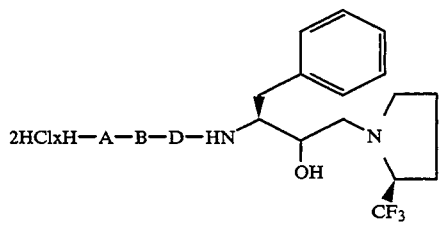

| Example No. | H—A—B—D— | Yield (%) | MS(FAB) m/e (M + H)+ | Rf/eluent ratio | Starting material from Example |
|---|---|---|---|---|---|
| 31 | H—Val— | 92 | 402 | 0.44, III(9:1) non-polar | 4 |
| 32 | H—Val— | 96 | 402 | 0.42, III(9:1) polar | 5 |
| 33 | H—Asn— | 94 | 417 | 0.01, I(9:1) non-polar | 7 |
| 34 | H—Asn— | 97 | 417 | 0.01, I(9:1) polar | 6 |
| 35 | H—Phe—Val— | 96 | 549 | 0.49, III(9:1) | 17 |

As described in Example 4, the following products (Table 6) were obtained by coupling the appropriate acids with the amine hydrochlorides:

TABLE 6

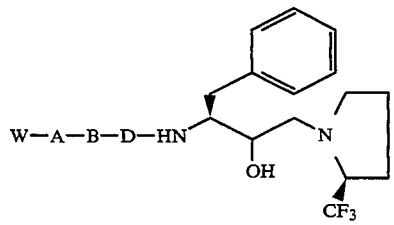

| Example No. | W—A—B—D— | Yield (%) | MS(FAB) m/e (M + H)+ | Rf/eluent ratio | Starting material from Example |
|---|---|---|---|---|---|
| 36 | ![quinoline]—CO—Asn— | 30 | 572 | 0.33, I(9:1) non-polar | 33 |
| 37 | ![quinoline]—CO—Asn— | 60 | 572 | 0.28, I(9:1) polar | 34 |
| 38 | ![indole]—CO—Asn— | 22 | 560 | 0.25, I(9:1) non-polar | 33 |
| 39 | ![indole]—CO—Asn— | 20 | 560 | 0.24, I(9:1) polar | 34 |

TABLE 6-continued

W—A—B—D—HN—CH(CH2Ph)—CH(OH)—CH2—N(pyrrolidine-2-CF3)

| Example No. | W—A—B—D— | Yield (%) | MS(FAB) m/e (M + H)+ | Rf/eluent ratio | Starting material from Example |
|---|---|---|---|---|---|
| 40 | (CH3)3C—O2S—CH2—CH(CH2-1-naphthyl)—CO—Asn— | 53 | 733 | 0.31, I(9:1) polar | 34 |
| 41 | (CH3)3C—O2S—CH2—CH(CH2-1-naphthyl)—CO—Asn— | 47 | 697 | 0.30, I(9:1) polar | 34 |
| 42 | (CH3)3C—CO—CH2—CH(CH2-1-naphthyl)—CO—Val— | 62 | 682 | 0.21, II(7:3) non-polar | 31 |
| 43 | (CH3)3C—CO—CH2—CH(CH2-1-naphthyl)—CO—Val— | 57 | 682 | 0.29, II(7:3) polar | 32 |
| 44 | Boc—Phe—Val | 52 | 649 | 0.18, I(95:5) non-polar | 2 |
| 45 | Boc—Ser—Phe—Val | 45 | 736 | 0.11, I(95:5) Melting point: 142° C. | 35 |

Example 46

1-{(2R and 2S, 3R,
4S)-3-[N-(tert-Butoxycarbonyl)amino]2,3-dihydroxy-5-phenylpentyl}-(2S)-2-(trifluoromethyl)pyrrolidine

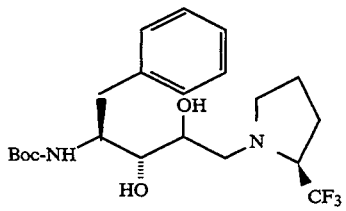

A solution of 450 mg (1.53 mmol) of the compound from Example LXVIII, 427 mg (3.07 mmol) of (2S)-2-(trifluoromethyl)pyrrolidine [cf. G. V. Shustov et al., Isvest. Akad. Nauk. SSSR, 1422 (1987); engl.] in 3 ml of n-propanol was stirred in a pressure vessel at 110° C. for 1 h. After cooling, the reaction mixture was concentrated in vacuo and, after a preliminary purification on 25 g of silica gel, separated by chromatography on 80 g of silica gel (toluene: ethyl acetate 7:3). 177 mg (27% of theory) of the non-polar diastereomer were obtained as a powder. $R_f$=0.30, II(7:3) MS(FAB): m/e=433 (M+H)+

In addition, 258 mg (39%) of the polar diastereomer were obtained as a powder. $R_f$=0.18, I(7:3) MS(FAB): m/e=433 (M+H)+

Example 47

1-{(2R and 2S, 3S,
4S)-3-[N-(tert-Butoxycarbonyl)amino]-2,3-dihydroxy-5-phenylpentyl}-(2S)-2-(trifluoromethyl) pyrrolidine

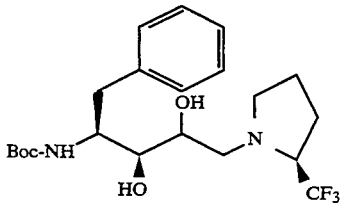

As described for Example 46, 1.70 g (46% of theory) of the non-polar diastereomer were obtained as crystals from 2.50 g (8.52 mmol) of the compound from Example LXIX and 2.37 g (17.04 mmol) of (2S)-2-(trifluoromethyl)pyrrolidine after chromatography of the crude product on 442 g of silica gel (toluene: acetonitrile 85:15). Melting point: from 103° C. (Dec.) $R_f$=0.27, II(7:3) MS(FAB): m/e=433 (M+H)+ as well as 923 mg (25% of theory) of the polar diastereomer as crystals. Melting point: 112° C. $R_f$=0.19, II(7:3) MS(FAB): m/e=433 (M+H) +

Example 48

1-{(2R and 2S, 3R,
4S)-3-[N-(tert-Butoxycarbonyl)amino]2,3-dihydroxy-5-phenylpentyl}-(2S)-2-(trifluoromethyl)piperidine

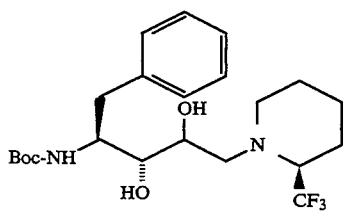

As described for Example 46, 218 mg (21% of theory) of the non-polar diastereomer were obtained as a syrup from 690 mg (2.35 mmol) of the compound from Example LXVIII and 720 mg (4.70 mmol) of (2S)-2-(trifluoromethyl)piperidine after chromatography of the crude product on 75 g of silica gel (toluene: acetonitrile 9:1). $R_f$=0.26, V(9:1) MS(FAB): m/e =447 (M+H)+

As well as 351 mg (33%) of the polar diasteromer as a syrup. $R_f$=0.06, V(9:1) MS(FAB): m/e=447 (M+H)+

As described for Example 2, the following amine hydrochlorides (Table 7) were obtained from the corresponding starting materials by removal of the tert-butoxycarbonyl protective group:

TABLE 7

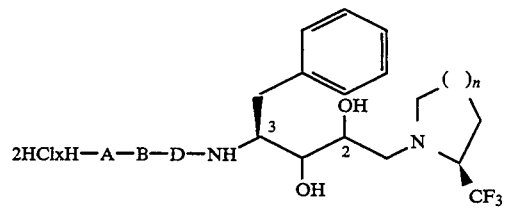

| Example No. | H—A—B—D— | n | 3-(OH) Stereochemistry | Yield (%) | MS(FAB) m/e (M + H)+ | $R_f$/eluent ratio | Starting material from Example/(isomer) |
|---|---|---|---|---|---|---|---|
| 48 | H— | 1 | R | 97 | 333 | 0.20, III(95:5) | 46 (non-polar) |
| 49 | H— | 1 | R | 96 | 333 | 0.20, III(95:5) | 46 (polar) |
| 50 | H— | 1 | S | 98 | 333 | 0.42, III(9:1) | 47 (non-polar) |
| 51 | H— | 1 | S | 94 | 333 | 0.41, III(9:1) | 47 (polar) |
| 52 | H— | 2 | R | 97 | 347 | 0.26, III(95:5) | 48 (non-polar) |
| 53 | H— | 2 | R | 95 | 347 | 0.24, III(95:5) | 48 (polar) |
| 54 | H—Val | 1 | R | 96 | 432 | 0.30, III(95:5) | 60 (non-polar) |
| 55 | H—Val | 1 | R | 98 | 432 | 0.29, III(95:5) | 60 (polar) |
| 56 | H—Val | 2 | R | 97 | 347 | 0.32, III(95:5) | 62 (non-polar) |
| 57 | H—Val | 2 | R | 99 | 347 | 0.30, III(95:5) | 63 (polar) |
| 58 | H—Asn | 1 | S | 96 | 447 | 0.30, III(9:1) | 65 (non-polar) |
| 59 | H—Asn | 1 | S | 98 | 447 | 0.27, III(9:1) | 67 (polar) |

As described for Examples 4 and 6, the following products (Table 8) were obtained by coupling of the appropriate acids with the amine hydrochlorides (starting materials):

TABLE 8

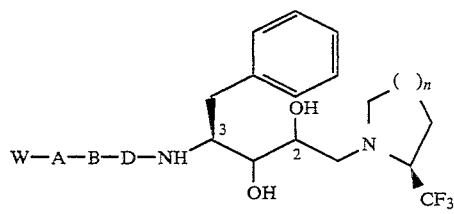

| Example No. | W—A—B—D— | n | 3-(OH) Stereochemistry | Yield (%) | MS(FAB) m/e (M + H)+ | Rf/eluent ratio Melting point [°C.] | Starting material from Example |
|---|---|---|---|---|---|---|---|
| 60 | Boc—Val | 1 | R | 81 | 532 | 0.27, III(3:2) amorphous | 48 |
| 61 | Boc—Val | 1 | R | 56 | 532 | 0.22, III(3:2) amorphous | 49 |
| 62 | Boc—Val | 2 | R | 74 | 546 | 0.25, III(7:3) amorphous | 52 |
| 63 | Boc—Val | 2 | R | 63 | 546 | 0.28, III(3:2) amorphous | 53 |
| 64 | Boc—NH—CH(CN)—CO | 1 | S | 8 | 529 | 0.38, I(95:5) 181 | 50 |
| 65 | Boc—Asn | 1 | S | 43 | 547 | 0.14, I(95:5) 212 | 50 |
| 66 | Boc—NH—CH(CN)—CO | 1 | S | 9 | 529 | 0.26, I(95:5) 173 | 51 |
| 67 | Boc—NH—CH(CN)—CO | 1 | S | 36 | 547 | 0.11, I(95:5) 145 | 51 |
| 68 | $(CH_3)_3C$—$SO_2$—CH($C_{10}H_7$)—CO—Val | 1 | R | 84 | 748 | 0.28, II(2:3) 163 | 54 |
| 69 | $(CH_3)_3C$—$SO_2$—CH($C_{10}H_7$)—CO—Val | 1 | R | 52 | 748 | 0.19, II(2:3) from 97 (dec.) | 55 |
| 70 | $(CH_3)_3C$—$SO_2$—CH($C_{10}H_7$)—CO—Val | 2 | R | 72 | 762 | 0.15, I(97:3) 155 | 62 |
| 71 | $(CH_3)_3C$—$SO_2$—CH($C_{10}H_7$)—CO—Val | 2 | R | 48 | 762 | 0.06, I(97:3) from 88 (dec.) | 63 |
| 72 | $(CH_3)_3C$—$SO_2$—CH($C_{10}H_7$)—CO—Asn | 1 | S | 62 | 763 | 0.22, I(97:3) 118 | 58 |
| 73 | $(CH_3)_3C$—$SO_2$—CH($C_{10}H_7$)—CO—Asn | 1 | S | 52 | 763 | 0.15, I(97:3) 110 | 59 |
| 74 | quinolin-2-yl—CO—Asn | 1 | S | 72 | 602 | 0.15, I(95:5) 190 | 58 |

TABLE 8-continued

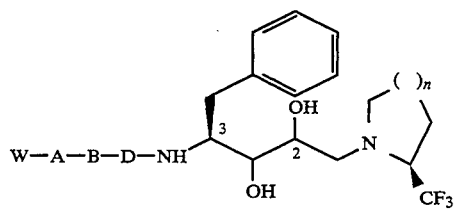

| Example No. | W—A—B—D— | n | 3-(OH) Stereo-chemistry | Yield (%) | MS(FAB) m/e (M + H)+ | Rf/eluent ratio Melting point [°C.] | Starting material from Example |
|---|---|---|---|---|---|---|---|
| 75 | 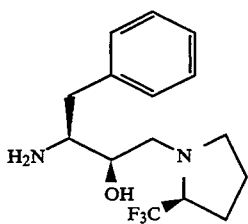 | 1 | S | 52 | 602 | 0.10, I(95:5) 137 | 59 |

Example 76

1-{(2R, 3S)-3-[(N-Benzyloxycarbonyl)amino]-2-hydroxy-4-phenylbutyl}-2-(trifluoromethyl)pyrrolidone

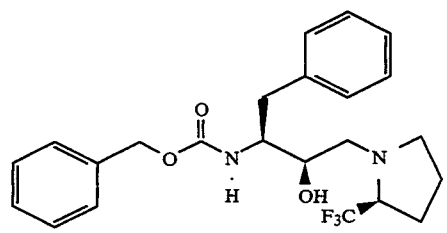

2 g of (2S)-2-(trifluoromethyl)pyrrolidine (14.4 mmol) and 4 g of the compound from Example LXXVIII (14.3 mmol) are dissolved in 8 ml of 2-propanol and stirred at 100° C. in a pressure tube. After 4 hours the reaction is complete. For working up, the mixture is diluted with 20 ml of dichloromethane and washed twice with water. The organic phase is dried and concentrated. Subsequent chromatographic purification (eluent: cyclohexane/acetone 3:1) gives 1.54 g of the title compound. Yield: 1.54 g (25% of theory) Rf=0.24 (cyclohexane/acetone 3:1)

Example 77

1-[(2R, 3S)-3-Amino-2-hydroxy-4-phenylbutyl]-(2S)-2-(trifluoromethyl)pyrrolidine

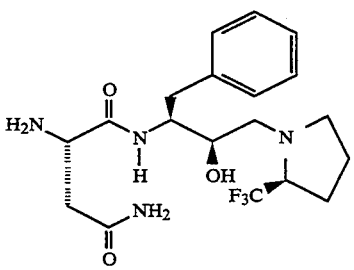

A solution of 1.5 g of the compound from Example 76 (3.5 mmol) in 10 ml of methanol is mixed with 200 mg of Pd-C (10%) and hydrogenated under normal pressure at room temperature. For working up, the catalyst is filtered off and concentrated. Yield: 1.0 g (96% of theory) Rf=0.2 (toluene/ethanol 3:1)

Example 78

1-{(2R, 3S)-3-[(N-Benzyloxycarbonyl-L-asparaginyl)amino]-2-hydroxy-4-phenylbutyl}-(2S)-2-(trifluoromethyl)pyrrolidine

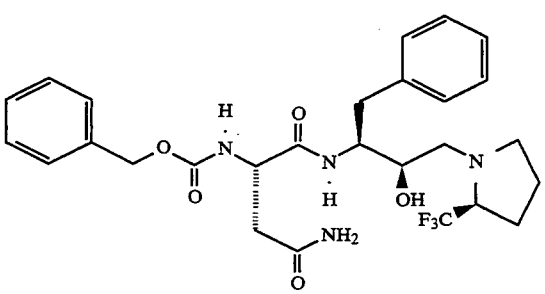

As described for Example 6, 800 mg of the title compound were obtained from the compound from Example 77 (3.6 mmol) after chromatographic purification of the crude product (eluent: dichloromethane/methanol 9:1). Yield: 800 mg (40% of theory) Rf=0.3 (dichloromethane/methanol 9:1) MS(FAB): m/e=551 (M+H)+

Example 79

1-{(2R,3S)-3-[(L-asparaginyl)amino]-2-hydroxy-4-phenylbutyl}-(2S)-2-(trifluoromethyl)pyrrolidine As described for Example 77,448 mg of the title compound were obtained from 700 mg of the compound from Example 78 (1.3 mmol) after chromatographic purification of the crude product (eluent: dichloromethane/methanol 9:1). Yield: 448 mg (83% of theory)

$R_f$=0.36 (dichloromethane/methanol 9:1) MS(FAB): m/e=417 (M+H)+

Example 80

1-{(2R, 3S)-3-[(N-Isoquinoline-2-carbonyl-L-asparaginyl)amino]-2-hydroxy-4-phenylbutyl}-(2S)-2-(trifluoromethyl)pyrrolidine

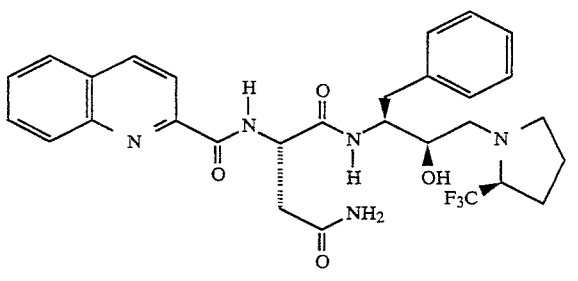

As described for Example 4, 390 mg of the title compound were obtained from 440 mg of the compound from Example 79 (1.1 mmol) after chromatographic purification of the crude product (eluent: toluene/ethanol 10:1). Yield: 339 mg (64% of theory) $R_f$=0.15 (toluene/ethanol 9:1) MS(FAB): m/e=572 (M+H)+

Example 81

2-{(2R, 3S)-3-[(N-Benzyloxycarbonyl)amino]-2-hydroxy-4-phenyl-butyl}(1S, 4aR, 8aR)-1-(trifluoromethyl)decahydroisoquinoline and

Example 82

2-{(2R, 3S)-3-[(N-Benzyloxycarbonyl)amino]-2-hydroxy-4-phenylbutyl}-(1R, 4aS, 8aS)-1-(trifluoromethyl)-decahydroisoquinoline

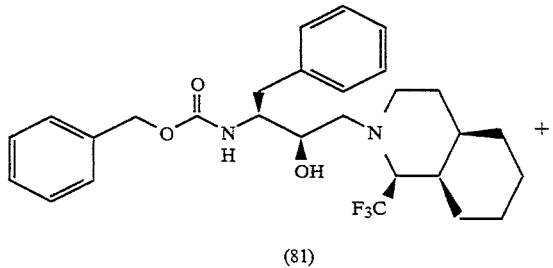

(81)

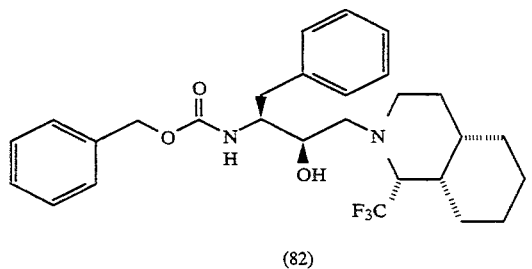

(82)

1.25 g of the 1:1 enantiomer pair (1S,4aR, 8aR)-1-(trifluoromethyl)-decahydroisoquinoline and (1R,4aS,-8aS)-1-(trifluoromethyl)-decahydroisoquinoline (6.0 mmol) and 1.7 g of the compound from Example LXXVIII (6.0 mmol) were reacted analogously to Example 76. Subsequent chromatographic separation of the diastereomers (eluent: toluene/ethyl acetate 5:1) gave 430 mg of Example 81 and 390 mg of Example 82. Yield: 430 mg of Example 81 (15% of theory) $R_f$=0.56 (toluene/ethanol 10:1) Yield: 390 mg of Example 82 (13% of theory) $R_f$=0.42 (toluene/ethanol 10:1)

Example 83

2-[(2R,3S)-3-Amino-2-hydroxy-4-phenylbutyl]-(1S,4aR,8aR) -(trifluoromethyl)-decahydroisoquinoline

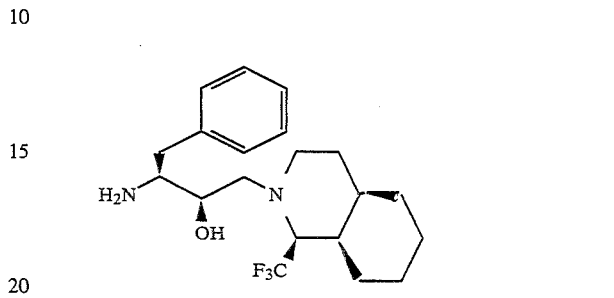

As described for Example 77, 277 mg of the title compound were obtained by hydrogenation of 400 mg of the compound from Example 81. Yield: 277 mg (94% of theory) $R_f$=0.24 (toluene/ethanol 10:1)

Example 84

2-[(2R,3S)-3-Amino-2-hydroxy-4-phenylbutyl]-(1R,4aS, 8aS) -1-(trifluoromethyl)-decahydroisoquinoline

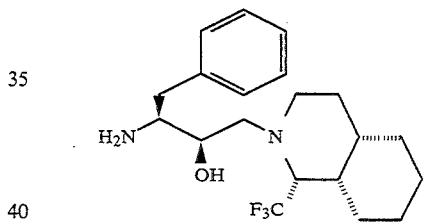

As described for Example 77, 249 mg of the title compound were obtained by hydrogenation of 360 mg of the compound from Example 82. Yield: 249 mg (94% of theory) $R_f$=0.19 (toluene/ethanol 10:1)

Example 85

2-{(2R,3S)-3-[(N-Benzyloxycarbonyl-L-asparaginyl-)amino]-2-hydroxy-4-phenylbutyl}-(1S, 4aR, 8aR)-1-(trifluoromethyl)-decahydroisoquinoline

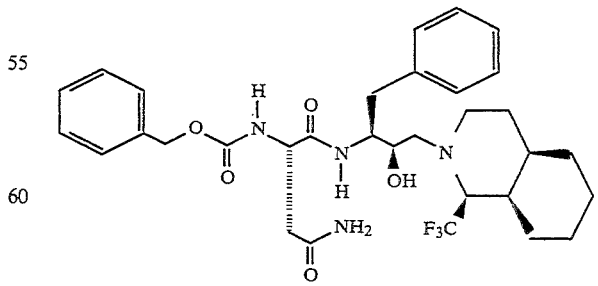

As described for Example 6, 275 mg of the title compound were obtained from 380 mg of the compound from Example 83 (1.0 mmol) after chromatographic purification of the crude product (eluent: toluene/e- thanol 10:1) Yield: 275 mg (43% of theory) $R_f=0.16$ (toluene/ethanol 10:1) MS (FAB): m/e=619 (M+H)+

Example 86

2-{(2R,3S)-3-[(N-Benzyloxycarbonyl-L-asparaginyl-)amino]-2-hydroxy-4-phenylbutyl}-(1R, 4aS, 8aS)-1-(trifluoromethyl)-decahydroisoquinoline

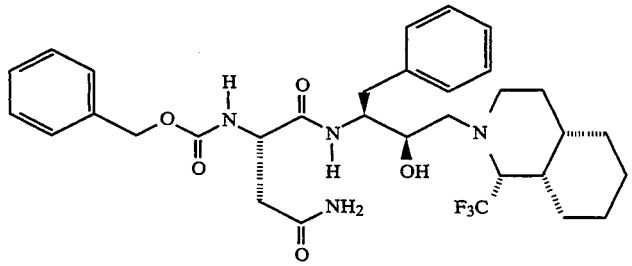

As described for Example 6, 130 mg of the title compound were obtained from 220 mg of compound from Example 83 (0.6 mmol) after chromatographic purification of the crude product (eluent: toluene/ethanol 10:1). Yield: 130 mg (37% of theory) $R_f=0.13$ (toluene/ethanol 10:1) MS (FAB): m/e=619 (M+H)+

Example 87

2-{(2R,3S)-3-[(L-asparaginyl)amino]-2-hydroxy-4-phenylbutyl}-(1S,4aR,8aR)-1-(trifluoromethyl)-decahydroisoquinoline

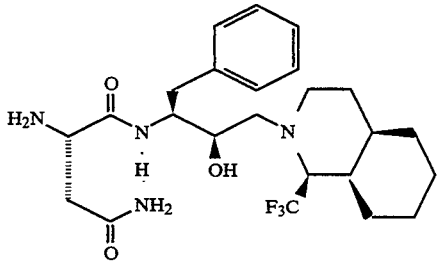

As described for Example 77, 200 mg of the title compound were obtained from 260 mg of the compound from Example 85 (0.4 mmol). Yield: 200 mg (98% of theory) $R_f=0.38$ (dichloromethane/methanol 9:1) MS (FAB): m/e=485 (M+H)+

Example 88

2-{(2R,3S)-3-[(L-asparaginyl)amino]-2-hydroxy-4-phenylbutyl}-(1R,4aS,8aS)-1-(trifluoromethyl)-decahydroisoquinoline

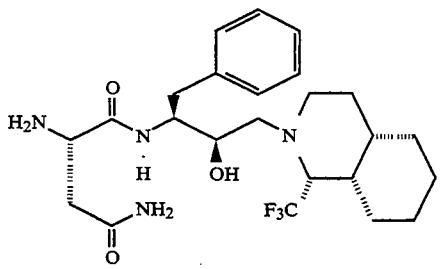

As described for Example 77, 132 mg of the title compound were obtained from 190 mg of the compound from Example 86 (0.3 mmol). Yield: 132 mg (98% of theory) $R_f=0.31$ (dichloromethane/methanol 9:1) MS (FAB): m/e=485 (M+H)+

Example 89

2-{(2R,3S)-3-[(N-Isoquinoline-2-carbonyl-L-asparaginyl)amino]-2-hydroxy-4-phenylbutyl}-(1S,4aR,8aR)-1-(trifluoromethyl)-decahydroisoquinoline

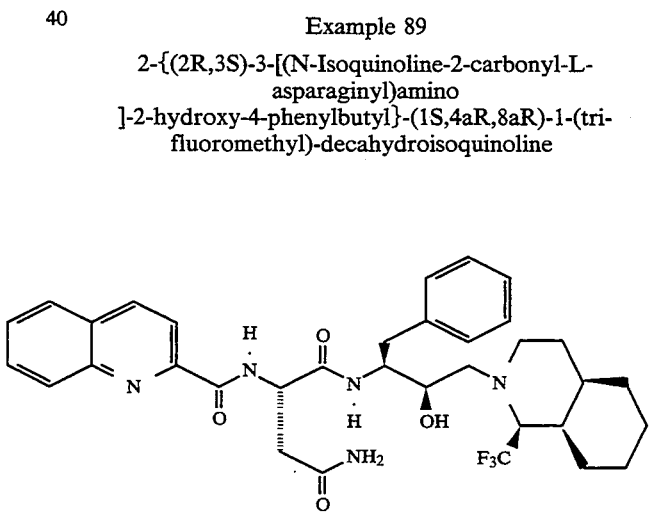

As described for Example 4, 133 mg of the title compound were obtained from 180 mg of the compound from Example 87 (372 μmol) after chromatographic purification of the crude product (eluent: toluene/ethanol 3:1). Yield: 133 mg (56% of theory) $R_f=0.48$ (toluene/ethanol 3:1) MS (FAB): m/e: 640 (M+H)+

Example 90

2-{(2R,3S)-3-[(N-Isoquinoline-2-carbonyl-L-asparaginyl)amino]-2-hydroxy-4-phenylbutyl}-(1R,4aS,8aS)-1(trifluoromethyl)-decahydroisoquinoline

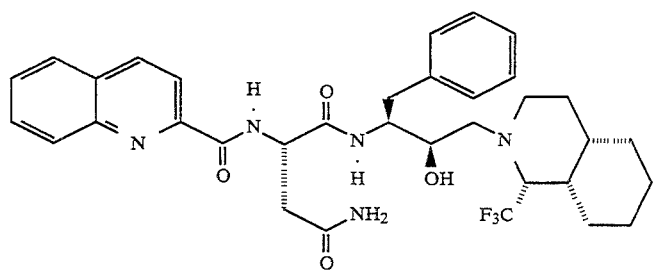

As described for Example 4, 69 mg of the title compound were obtained from 110 mg of the compound from Example 88 (227 μmol) after chromatographic purification of the crude product (eluent: toluene/ethanol 3:1) Yield: 69 mg (48% of theory) $R_f=0.41$ (toluene/ethanol 3:1) MS (FAB): m/e: 640 (M+H)+

Example 91

1-{(2R,3S)-3-[(N-Benzyloxycarbonyl)amino]-2-hydroxy-4-phenylbutyl}-(2S,5R)-5-methyl-2-(trifluoromethyl)pyrrolidine and

Example 92

1-{(2R,3S)-3-[(N-Benzyloxycarbonyl)amino]-2-hydroxy-4-phenylbutyl}-(2R,5S)-5-methyl-2-(trifluoromethyl)pyrrolidine

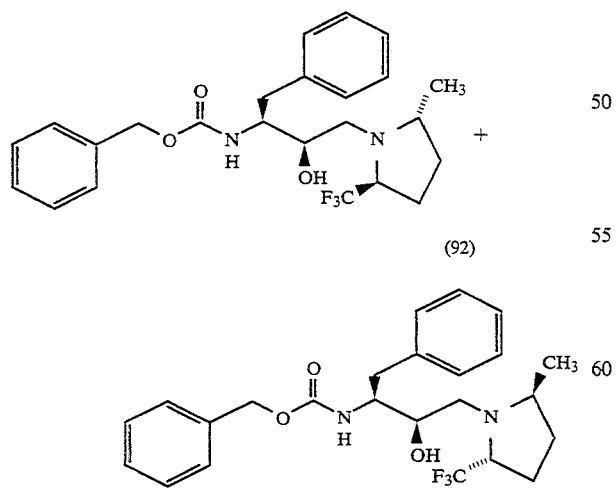

2 g of the 1:1 enantiomer pair (2S,5R)-5-methyl-2-(trifluoromethyl)-pyrrolidine and (2S,5R)-5-methyl-2-(trifluoromethyl)-pyrrolidine (13.1 mmol) and 3.66 g of the compound from Example LXXVIII (13.1 mmol) were reacted analogously to Example 76. Subsequent chromatographic purification (eluent: cyclohexane/acetone 3:1) gave 2.1 g of the diastereomer pair of the title compounds. Yield: 2.1 g (36% of theory) $R_f=0.52$ (toluene/ethanol 10:1)

Example 93

1-{(2R,3S)-3-Amino-2-hydroxy-4-phenylbutyl}-(2S,5R)-5-methyl-2-(trifluoromethyl)-pyrrolidine and

Example 94

1-{(2R,3S)-3-Amino-2-hydroxy-4-phenylbutyl}-(2R,5S)-5-methyl-2-(trifluoromethyl)-pyrrolidine

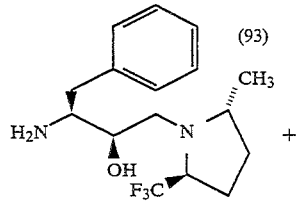

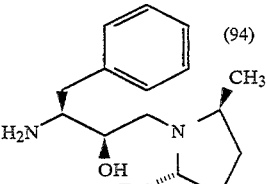

2 g of the diastereomer pair of the compounds 91 and 92 (4.4 mmol) were hydrogenated analogously to Example 77. Yield: 1.38 g (98% of theory) $R_f=0.20$ (toluene/ethanol 10:1)

Example 95

1-{(2R,3S)-3-[(N-Benzyloxycarbonyl-L-asparaginyl-)amino]-2-hydroxy-4-phenylbutyl}-(2S,5R)-5-methyl-2-(trifluoromethyl)pyrrolidine and

Example 96

1-{(2R,3S)-3-[(N-Benzyloxycarbonyl-L-asparaginyl-)amino]-2-hydroxy-4-phenylbutyl}-(2R,5S)-5-methyl-2-(trifluoromethyl)pyrrolidine

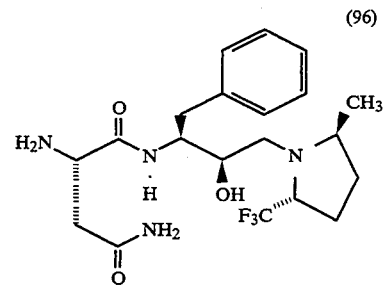
(96)

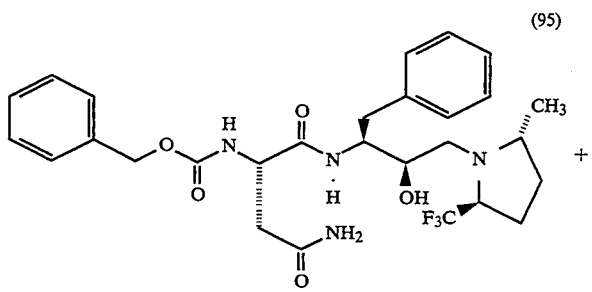
(95)

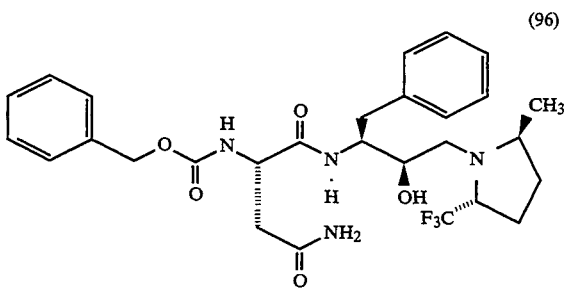
(96)

As described for Example 6, 1.08 g of the title compound were obtained from 1.38 g of the compounds from Examples 93 and 94 (4.4 mmol) after chromatographic purification of the crude product (eluent: toluene/ ethanol 10:1) Yield: 1.08 g (44% of theory) $R_f=0.13$ (toluene/ethanol 10:1) MS (FAB): m/e=565 (M+H)+

Example 97

1-{(2R,3S)-3-[(L-asparaginyl)amino]-2-hydroxy-4-phenylbutyl}-(2S,5R)-5-methyl-2-(trifluoromethyl)pyrrolidine and

Example 98

1-{(2R,3S)-3-[(L-asparaginyl)amino]-2-hydroxy-4-phenylbutyl}-(2R,5S)-5-methyl-2-(trifluoromethyl)pyrrolidine

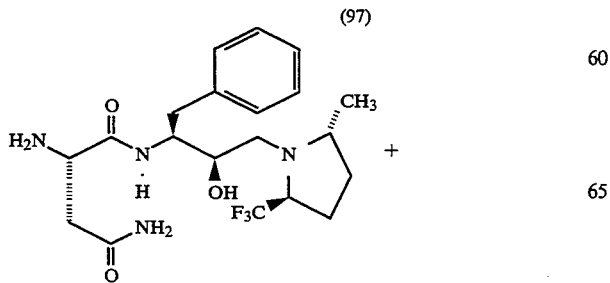
(97)

As described for Example 77, 725 mg of the title compound were obtained from 980 mg of the compounds 95 and 96 (1.7 mmol). Yield: 725 mg (99% of theory) $R_f=0.32$ (dichloromethane/methanol 9:1) MS (FAB): m/e=431 (M+H)+

Example 99

1-{(2R,3S)-3-[(N-Isoquinoline-2-carbonyl-L-asparaginyl-)amino]-2-hydroxy-4-phenylbutyl}-(2S,5R)-5-methyl-2-(trifluoromethyl)pyrrolidine and

Example 100

1-{(2R,3S)-3-[(N-Isoquinoline-2-carbonyl-L-asparaginyl-)amino]-2-hydroxy-4-phenylbutyl}-(2R,5S)-5-methyl-2-(trifluoromethyl)pyrrolidine

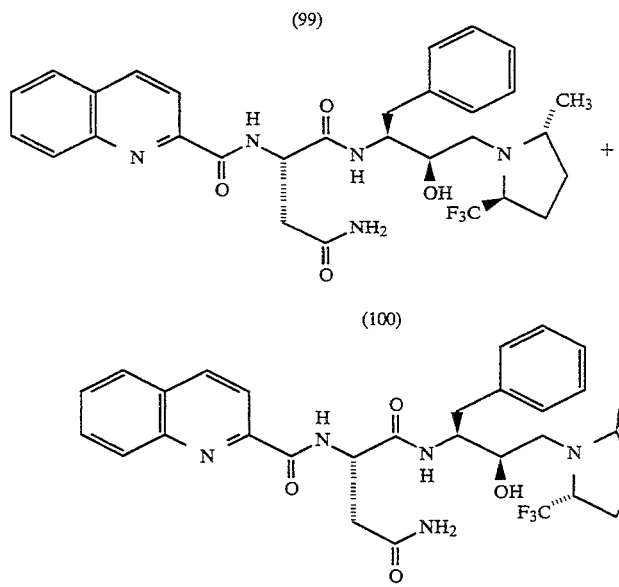

As described for Example 4, 700 mg of the title compound were obtained from 729 mg of the compounds 97 and 98 (1.7 mmol) after chromatographic purification of the crude product (eluent: toluene/ethanol 10:1). Yields 700 mg (70% of theory) $R_f$=0.18 (toluene/ethanol 10:1) MS (FAB): m/e=586 (M+H)+.

We claim:

1. A compound of the formula:

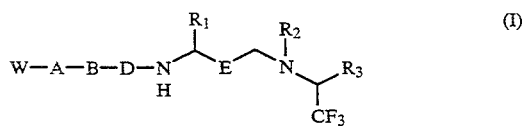

in which

W represents a group of the formula $R^4$—CO—;
in which $R^4$ represents a radical of the formula:

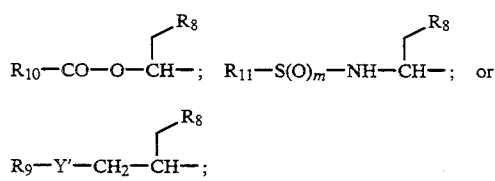

which $R_8$ represents phenyl or naphthyl;
$R_9$, $R_{10}$ and $R_{11}$ independently represent straight-chain or branched alkyl having up to 14 carbon atoms, which is optionally substituted by phenyl or naphthyl, or benzyloxy or aryl having 6 to 10 carbon atoms, which is in turn substituted by alkyl having up to 4 carbon atoms;
Y' represents CO or $SO_2$;
m represents a number 0, 1 or 2;
A, B and D together represent a radical of the formula:

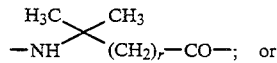

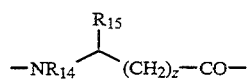

in which
r represents a number 0 or 1;
$R_{14}$ represents hydrogen or straight-chain or branched alkyl having up to 4 carbon atoms;
$R_{15}$ represents cycloalkyl having 3 to 8 carbon atoms or aryl having 6 to 10 carbon atoms or hydrogen, or represents straight-chain or branched alkyl having up to 8 carbon atoms;
z represents the number 0 or 1;
$R_1$ represents straight-chain or branched alkyl or alkenyl having up to 10 carbon atoms which are optionally, substituted by cycloalkyl having 3 to 8 carbon atoms or aryl having 6 to 10 carbon atoms, each of which can in turn be substituted by halogen, nitro, hydroxyl, amino or straight-chain or branched alkoxy having up to 4 carbon atoms;
E represents a radical of the formula:

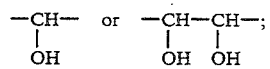

$R_2$ and $R_3$, together with the nitrogen atom and including the group:

form a heterocycle of the formula

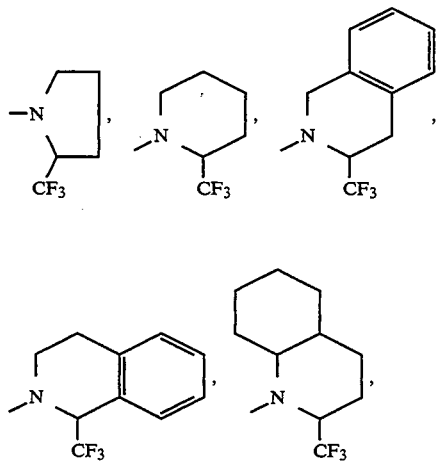
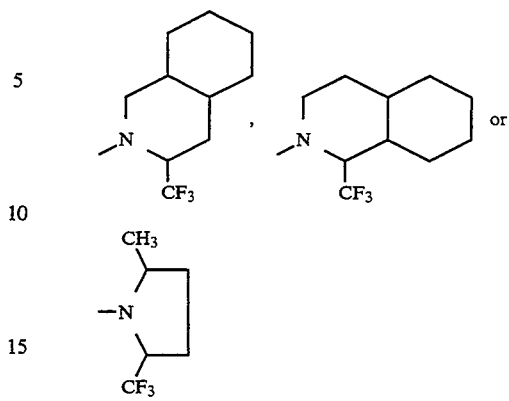
-continued
which is optionally substituted by straight-chain or branched alkyl having up to 8 carbon atoms; or physiologically acceptable salt thereof.
* * * * *

UNITED STATES PATENT AND TRADEMARK OFFICE
CERTIFICATE OF CORRECTION

PATENT NO. : 5,430,151
DATED : July 4, 1995
INVENTOR(S) : Habich, et al.

It is certified that error appears in the above-indentified patent and that said Letters Patent is hereby corrected as shown below:

Col. 65, line 64  Before " which " insert -- in --

Col. 66, line 43  Delete " cydoalkyl " and substitute -- cycloalkyl --

Signed and Sealed this

Twenty-sixth Day of November 1996

Attest:

BRUCE LEHMAN

*Attesting Officer*     *Commissioner of Patents and Trademarks*